United States Patent
Li

(10) Patent No.: US 7,820,435 B2
(45) Date of Patent: Oct. 26, 2010

(54) DE NOVO SYNTHESIZED PLASMID, METHODS OF MAKING AND USE THEREOF

(75) Inventor: Chuan Li, San Diego, CA (US)

(73) Assignee: Expression Technologies Inc., San Diego, CA (US)

( * ) Notice: Subject to any disclaimer, the term of this patent is extended or adjusted under 35 U.S.C. 154(b) by 0 days.

(21) Appl. No.: 10/068,664

(22) Filed: Feb. 6, 2002

(65) Prior Publication Data

US 2003/0157661 A1    Aug. 21, 2003

(51) Int. Cl.
*C12N 15/00*     (2006.01)
(52) U.S. Cl. .............................. 435/320.1; 435/252.33; 435/325
(58) Field of Classification Search .............. 435/320.1, 435/91.41, 91.52
See application file for complete search history.

(56) References Cited

U.S. PATENT DOCUMENTS

| | | | |
|---|---|---|---|
| 5,928,897 A * | 7/1999 | Lereclus | 435/69.1 |
| 6,387,662 B1 | 5/2002 | Liang et al. | |
| 6,464,972 B1 | 10/2002 | Gromeier et al. | |
| 6,497,873 B1 * | 12/2002 | Whitt et al. | 424/93.2 |

OTHER PUBLICATIONS

Sutcliffe, Nucleic Acids Res. 1978, 5:2721-8.*
Smith, Ho et al, Generating a synthetic genome by whole genome assembly: . . . , PNAS, Dec. 23, 2003, 15440-15445, 100,26.
Cello, J et al, Chemical Sythesis of Poliovirus cDNA: Generation of Infectious Virus in the Absence of . . . , Science Aug. 9, 2002, 1016-1018, 297.
Stemmer, WPC et al, Single-step assembly of a gene and entire plasmid from large number of . . . , Gene (1995) 49-53, 164.

* cited by examiner

*Primary Examiner*—James S Ketter

(57) ABSTRACT

The invention relates to a de novo synthesized plasmid. The plasmid comprises relevant sequences for plasmid replication and plasmid selection. The methods of making and use of the plasmid are disclosed. The plasmid can be used to make other plasmids. These plasmids and their host cells can be used for biomedical applications.

5 Claims, 5 Drawing Sheets

SEQUENCE LISTING

```
<160> NUMBER OF SEQ ID NOS: 41

<210> SEQ ID NO 1
<211> LENGTH: 44
<212> TYPE: DNA
<213> ORGANISM: Artificial sequence
<220> FEATURE:
<223> OTHER INFORMATION: Primer

<400> SEQUENCE: 1
cgcccgccgc ccgggcgccc cgccttccgc ttcctcgctc actg            44

<210> SEQ ID NO 2
<211> LENGTH: 44
<212> TYPE: DNA
<213> ORGANISM: Artificial sequence
<220> FEATURE:
<223> OTHER INFORMATION: Primer

<400> SEQUENCE: 2
```

-continued cgcccgccgc ccgggcgccc cgccaacgcg gaagtcagcg ccct            44

<210> SEQ ID NO 3
<211> LENGTH: 44
<212> TYPE: DNA
<213> ORGANISM: Artificial sequence
<220> FEATURE:
<223> OTHER INFORMATION: Primer

<400> SEQUENCE: 3
cgcccgccgc ccgggcgccc cgccaacgca gaccgttccg tggc            44

<210> SEQ ID NO 4
<211> LENGTH: 32
<212> TYPE: DNA
<213> ORGANISM: Artificial sequence
<220> FEATURE:
<223> OTHER INFORMATION: Primer

<400> SEQUENCE: 4
ccgccgcgcc gcttccactg agcgtcagac cc                         32

<210> SEQ ID NO 5
<211> LENGTH: 32
<212> TYPE: DNA
<213> ORGANISM: Artificial sequence
<220> FEATURE:
<223> OTHER INFORMATION: Primer

<400> SEQUENCE: 5
gggcggcggg cgttcgggga aatgtgcgcg ga                         32

<210> SEQ ID NO 6
<211> LENGTH: 32
<212> TYPE: DNA
<213> ORGANISM: Artificial sequence
<220> FEATURE:
<223> OTHER INFORMATION: Primer

<400> SEQUENCE: 6
gggcggcggg cgttgtcggg aagatgcgtg at                         32

<210> SEQ ID NO 7
<211> LENGTH: 32
<212> TYPE: DNA
<213> ORGANISM: Artificial sequence
<220> FEATURE:
<223> OTHER INFORMATION: Primer

<400> SEQUENCE: 7
gggcggcggg cgttctcatg tttgacagct ta                         32

<210> SEQ ID NO 8
<211> LENGTH: 32
<212> TYPE: DNA
<213> ORGANISM: Artificial sequence
<220> FEATURE:
<223> OTHER INFORMATION: Primer

<400> SEQUENCE: 8
gggcggcggg cgaagccact ggagcacctc aa                         32

<210> SEQ ID NO 9
<211> LENGTH: 32
<212> TYPE: DNA
<213> ORGANISM: Artificial sequence

```
<220> FEATURE:
<223> OTHER INFORMATION: Primer

<400> SEQUENCE: 9
gcggcgcggc ggtacggggt ctgacgctca gt                                    32

<210> SEQ ID NO 10
<211> LENGTH: 32
<212> TYPE: DNA
<213> ORGANISM: Artificial sequence
<220> FEATURE:
<223> OTHER INFORMATION: Primer

<400> SEQUENCE: 10
gcggcgcggc ggatcgcccc atcatccagc ca                                    32

<210> SEQ ID NO 11
<211> LENGTH: 32
<212> TYPE: DNA
<213> ORGANISM: Artificial sequence
<220> FEATURE:
<223> OTHER INFORMATION: Primer

<400> SEQUENCE: 11
gcggcgcggc ggttcacgtt cgctcgcgta tc                                    32

<210> SEQ ID NO 12
<211> LENGTH: 32
<212> TYPE: DNA
<213> ORGANISM: Artificial sequence
<220> FEATURE:
<223> OTHER INFORMATION: Primer

<400> SEQUENCE: 12
gcggcgcggc ggaagcacac ggtcacactg ct                                    32

<210> SEQ ID NO 13
<211> LENGTH: 32
<212> TYPE: DNA
<213> ORGANISM: Artificial sequence
<220> FEATURE:
<223> OTHER INFORMATION: Primer

<400> SEQUENCE: 13
ggcggggcgc ccaccatcga atggtgcaaa ac                                    32

<210> SEQ ID NO 14
<211> LENGTH: 44
<212> TYPE: DNA
<213> ORGANISM: Artificial sequence
<220> FEATURE:
<223> OTHER INFORMATION: Primer

<400> SEQUENCE: 14
cgcccgccgc ccgggccgcg cccgtgccta atgagtgagc taac                       44

<210> SEQ ID NO 15
<211> LENGTH: 32
<212> TYPE: DNA
<213> ORGANISM: Artificial sequence
<220> FEATURE:
<223> OTHER INFORMATION: Primer

<400> SEQUENCE: 15
cgggcgcggc ccataaaagc ggcttcctga ca                                    32
```

<210> SEQ ID NO 16
<211> LENGTH: 39
<212> TYPE: DNA
<213> ORGANISM: Artificial sequence
<220> FEATURE:
<223> OTHER INFORMATION: Primer

<400> SEQUENCE: 16
gcaaaacaaa acggcctcct gtcaggaagc cgcttttat                    39

<210> SEQ ID NO 17
<211> LENGTH: 44
<212> TYPE: DNA
<213> ORGANISM: Artificial sequence
<220> FEATURE:
<223> OTHER INFORMATION: Primer

<400> SEQUENCE: 17
ggaggccgtt ttgttttgct cgaaattaat acgactcact atag              44

<210> SEQ ID NO 18
<211> LENGTH: 50
<212> TYPE: DNA
<213> ORGANISM: Artificial sequence
<220> FEATURE:
<223> OTHER INFORMATION: Primer

<400> SEQUENCE: 18
ggaattgtta tccgctcaca attccctata gtgagtcgta ttaatttcga        50

<210> SEQ ID NO 19
<211> LENGTH: 42
<212> TYPE: DNA
<213> ORGANISM: Artificial sequence
<220> FEATURE:
<223> OTHER INFORMATION: Primer

<400> SEQUENCE: 19
ggaattgtga gcggataaca attcctaatt ttgtttaact tt                42

<210> SEQ ID NO 20
<211> LENGTH: 34
<212> TYPE: DNA
<213> ORGANISM: Artificial sequence
<220> FEATURE:
<223> OTHER INFORMATION: Primer

<400> SEQUENCE: 20
atgtatatct ccttcttaaa gttaaacaaa atta                         34

<210> SEQ ID NO 21
<211> LENGTH: 50
<212> TYPE: DNA
<213> ORGANISM: Artificial sequence
<220> FEATURE:
<223> OTHER INFORMATION: Primer

<400> SEQUENCE: 21
aagaaggaga tatacatatg aagcttcccg ggtaccggtc gactagttaa        50

<210> SEQ ID NO 22
<211> LENGTH: 58
<212> TYPE: DNA
<213> ORGANISM: Artificial sequence
<220> FEATURE:
<223> OTHER INFORMATION: Primer

<400> SEQUENCE: 22
tagaggcccc aagggttat gctagttaac tagtcgaccg gtacccggga agcttcat        58

<210> SEQ ID NO 23
<211> LENGTH: 50
<212> TYPE: DNA
<213> ORGANISM: Artificial sequence
<220> FEATURE:
<223> OTHER INFORMATION: Primer

<400> SEQUENCE: 23
ctagcataac cccttgggcc tctaaacggg gtcttgaggg gttttttgca        50

<210> SEQ ID NO 24
<211> LENGTH: 37
<212> TYPE: DNA
<213> ORGANISM: Artificial sequence
<220> FEATURE:
<223> OTHER INFORMATION: Primer

<400> SEQUENCE: 24
cgcccgccgc cctgcaaaaa acccctcaag accgtt        37

<210> SEQ ID NO 25
<211> LENGTH: 230
<212> TYPE: DNA
<213> ORGANISM: Artificial sequence
<220> FEATURE:
<223> OTHER INFORMATION: Sequence is synthesized.

<400> SEQUENCE: 25
cgggcgcggc ccataaaagc ggcttcctga caggaggccg ttttgttttg ctcgaaatta        60
atacgactca ctatagggaa ttgtgagcgg ataacaattc ctaattttgt ttaactttaa       120
gaaggagata tacatatgaa gcttcccggg taccggtcga ctagttaact agcataaccc       180 cttgggcct ctaaacgggt cttgagggt ttttttgcagg gcggcgggcg                    230

<210> SEQ ID NO 26
<211> LENGTH: 32
<212> TYPE: DNA
<213> ORGANISM: Artificial sequence
<220> FEATURE:
<223> OTHER INFORMATION: Primer

<400> SEQUENCE: 26
ggcggggcgc ccttcccct tgaaggggcg aa        32

<210> SEQ ID NO 27
<211> LENGTH: 44
<212> TYPE: DNA
<213> ORGANISM: Artificial sequence
<220> FEATURE:
<223> OTHER INFORMATION: Primer

<400> SEQUENCE: 27
cgcccgccgc ccgggccgcg cccgatgagc tggacgcact cgcg        44

<210> SEQ ID NO 28
<211> LENGTH: 35
<212> TYPE: DNA
<213> ORGANISM: Artificial sequence
<220> FEATURE:
<223> OTHER INFORMATION: Primer -continued

<400> SEQUENCE: 28
gaaggagata tacatatgaa tattcgtcca ttgca                                35

<210> SEQ ID NO 29
<211> LENGTH: 36
<212> TYPE: DNA
<213> ORGANISM: Artificial sequence
<220> FEATURE:
<223> OTHER INFORMATION: Primer

<400> SEQUENCE: 29
ctagttaact agtcgattac atcatgccgc ccatgc                               36

<210> SEQ ID NO 30
<211> LENGTH: 32
<212> TYPE: DNA
<213> ORGANISM: Artificial sequence
<220> FEATURE:
<223> OTHER INFORMATION: Primer

<400> SEQUENCE: 30
ggcggggcgc ccgcgggata tccggatata gt                                   32

<210> SEQ ID NO 31
<211> LENGTH: 32
<212> TYPE: DNA
<213> ORGANISM: Artificial sequence
<220> FEATURE:
<223> OTHER INFORMATION: Primer

<400> SEQUENCE: 31
cgcccgccgc ccggtgccta atgagtgagc ta                                   32

<210> SEQ ID NO 32
<211> LENGTH: 2701
<212> TYPE: DNA
<213> ORGANISM: Artificial sequence
<220> FEATURE:
<223> OTHER INFORMATION: Sequence is a de novo synthesized plasmid.

<400> SEQUENCE: 32
ccgccgcgcc gcttccactg agcgtcagac cccgtagaaa agatcaaagg atcttcttga     60
gatcctttt ttctgcgcgt aatctgctgc ttgcaaacaa aaaaaccacc gctaccagcg     120
gtggtttgtt tgccggatca agagctacca actctttttc cgaaggtaac tggcttcagc    180
agagcgcaga taccaaatac tgtccttcta gtgtagccgt agttaggcca ccacttcaag    240
aactctgtag caccgcctac atacctcgct ctgctaatcc tgttaccagt ggctgctgcc    300
agtggcgata agtcgtgtct taccgggttg gactcaagac gatagttacc ggataaggcg    360
cagcggtcgg gctgaacggg gggttcgtgc acacagccca gcttggagcg aacgacctac    420
accgaactga gatacctaca gcgtgagcta tgagaaagcg ccacgcttcc gaagggaga    480
aaggcggaca ggtatccggt aagcggcagg gtcggaacag gagagcgcac gagggagctt    540
ccagggggaa acgcctggta tctttatagt cctgtcgggt ttcgccacct ctgacttgag    600
cgtcgatttt tgtgatgctc gtcagggggg cggagcctat ggaaaaacgc cagcaacgcg    660
gcctttttac ggttcctggc cttttgctgg ccttttgctc acatgttctt tcctgcgtta    720
tcccctgatt ctgtggataa ccgtattacc gcctttgagt gagctgatac cgctcgccgc    780
agccgaacga ccgagcgcag cgagtcagtg agcgaggaag cggaagagcg cctgatgcgg    840
tatttctcc ttacgcatct gtgcggtatt tcacaccgca tatggtgcac tctcagtaca    900

| | |
|---|---:|
| atctgctctg atgccgcata gttaagccag tatacactcc gctatcgcta cgtgactggg | 960 |
| tcatggctgc gccccgacac ccgccaacac ccgctgacgc gccctgacgg gcttgtctgc | 1020 |
| tcccggcatc cgcttacaga caagctgtga ccgtctccgg gagctgcatg tgtcagaggt | 1080 |
| tttcaccgtc atcaccgaaa cgcgcgaggc agctgcggta aagctcatca gcgtggtcgt | 1140 |
| gaagcgattc acagatgtct gcctgttcat ccgcgtccag ctcgttgagt ttctccagaa | 1200 |
| gcgttaatgt ctggcttctg ataaagcggg ccatgttaag ggcggttttt tcctgtttgg | 1260 |
| tcactgatgc ctccgtgtaa gggggatttc tgttcatggg ggtaatgata ccgatgaaac | 1320 |
| gagagaggat gctcacgata cgggttactg atgatgaaca tgcccggtta ctggaacgtt | 1380 |
| gtgagggtaa acaactggcg gtatggatgc ggcgggacca gagaaaaatc actcagggtc | 1440 |
| aatgccagcg cttcgttaat acagatgtag gtgttccaca gggtagccag cagcatcctg | 1500 |
| cgatgcagat ccggaacata atggtgcagg gcgctgactt ccgcgttggc ggggcgcccg | 1560 |
| ggcggcgggc gttcggggaa atgtgcgcgg aacccctatt tgtttatttt tctaaataca | 1620 |
| ttcaaatatg tatccgctca tgagacaata accctgataa atgcttcaat aatattgaaa | 1680 |
| aaggaagagt atgagtattc aacatttccg tgtcgccctt attcccttttt ttgcggcatt | 1740 |
| ttgccttcct gttttttgctc acccagaaac gctggtgaaa gtaaaagatg ctgaagatca | 1800 |
| gttgggtgca cgagtgggtt acatcgaact ggatctcaac agcggtaaga tccttgagag | 1860 |
| ttttcgcccc gaagaacgtt ttccaatgat gagcactttt aaagttctgc tatgtggcgc | 1920 |
| ggtattatcc cgtattgacg ccgggcaaga gcaactcggt cgccgcatac actattctca | 1980 |
| gaatgacttg gttgagtact caccagtcac agaaaagcat cttacggatg gcatgacagt | 2040 |
| aagagaatta tgcagtgctg ccataaccat gagtgataac actgcggcca acttacttct | 2100 |
| gacaacgatc ggaggaccga aggagctaac cgcttttttg cacaacatgg gggatcatgt | 2160 |
| aactcgcctt gatcgttggg aaccggagct gaatgaagcc ataccaaacg acgagcgtga | 2220 |
| caccacgatg cctgtagcaa tggcaacaac gttgcgcaaa ctattaactg gcgaactact | 2280 |
| tactctagct tcccggcaac aattaataga ctggatggag gcggataaag ttgcaggacc | 2340 |
| acttctgcgc tcggcccttc cggctggctg gtttattgct gataaatctg gagccggtga | 2400 |
| gcgtgggtct cgcggtatca ttgcagcact ggggccagat ggtaagccct cccgtatcgt | 2460 |
| agttatctac acgacgggga gtcaggcaac tatggatgaa cgaaatagac agatcgctga | 2520 |
| gataggtgcc tcactgatta agcattggta actgtcagac caagtttact catatatact | 2580 |
| ttagattgat ttaaaacttc atttttaatt taaaaggatc taggtgaaga tcctttttga | 2640 |
| taatctcatg accaaaatcc cttaacgtga gttttcgttc cactgagcgt cagaccccgt | 2700 |
| a | 2701 |

<210> SEQ ID NO 33
<211> LENGTH: 1979
<212> TYPE: DNA
<213> ORGANISM: Artificial sequence
<220> FEATURE:
<223> OTHER INFORMATION: Sequence is a de novo synthesized plasmid.

<400> SEQUENCE: 33

| | |
|---|---:|
| ccgccgcgcc gcttccactg agcgtcagac cccgtagaaa agatcaaagg atcttcttga | 60 |
| gatccttttt ttctgcgcgt aatctgctgc ttgcaaacaa aaaaaccacc gctaccagcg | 120 |
| gtggtttgtt tgccggatca agagctacca actcttttc cgaaggtaac tggcttcagc | 180 |

```
agagcgcaga taccaaatac tgtccttcta gtgtagccgt agttaggcca ccacttcaag      240
aactctgtag caccgcctac atacctcgct ctgctaatcc tgttaccagt ggctgctgcc      300
agtggcgata agtcgtgtct taccggggttg gactcaagac gatagttacc ggataaggcg     360
cagcggtcgg gctgaacggg gggttcgtgc acacagccca gcttggagcg aacgacctac      420
accgaactga gatacctaca gcgtgagcta tgagaaagcg ccacgcttcc cgaagggaga      480
aaggcggaca ggtatccggt aagcggcagg gtcggaacag gagagcgcac gagggagctt      540 ccaggggggaa acgcctggta tctttatagt cctgtcgggt ttcgccacct ctgacttgag     600
cgtcgatttt tgtgatgctc gtcagggggg cggagcctat ggaaaaacgc cagcaacgcg      660
gcctttttac ggttcctggc cttttgctgg ccttttgctc acatgttctt tcctgcgtta      720
tcccctgatt ctgtggataa ccgtattacc gcctttgagt gagctgatac cgctcgccgc      780
agccgaacga ccgagcgcag cgagtcagtg agcgaggaag cggaaggcgg ggcgcccggg      840
cggcgggcgt tcggggaaat gtgcgcggaa cccctatttg tttatttttc taaatacatt      900
caaatatgta tccgctcatg agacaataac cctgataaat gcttcaataa tattgaaaaa      960
ggaagagtat gagtattcaa catttccgtg tcgcccttat tcccttttt gcggcatttt      1020 gccttcctgt ttttgctcac ccagaaacgc tggtgaaagt aaaagatgct gaagatcagt      1080
tgggtgcacg agtgggttac atcgaactgg atctcaacag cggtaagatc cttgagagtt      1140
ttcgccccga agaacgtttt ccaatgatga gcacttttaa agttctgcta tgtggcgcgg      1200
tattatcccg tattgacgcc gggcaagagc aactcggtcg ccgcatacac tattctcaga      1260
atgacttggt tgagtactca ccagtcacag aaaagcatct tacggatggc atgacagtaa      1320
gagaattatg cagtgctgcc ataaccatga gtgataacac tgcggccaac ttacttctga      1380
caacgatcgg aggaccgaag gagctaaccg cttttttgca acatggggg atcatgtaa      1440 ctcgccttga tcgttgggaa ccggagctga atgaagccat accaaacgac gagcgtgaca      1500
ccacgatgcc tgtagcaatg gcaacaacgt tgcgcaaact attaactggc gaactactta      1560
ctctagcttc ccggcaacaa ttaatagact ggatggaggc ggataaagtt gcaggaccac      1620
ttctgcgctc ggcccttccg gctggctggt ttattgctga taaatctgga gccggtgagc      1680
gtgggtctcg cggtatcatt gcagcactgg ggccagatgg taagccctcc cgtatcgtag      1740
ttatctacac gacggggagt caggcaacta tggatgaacg aaatagacag atcgctgaga      1800
taggtgcctc actgattaag cattggtaac tgtcagacca agtttactca tatatacttt      1860
agattgattt aaaacttcat ttttaattta aaaggatcta ggtgaagatc cttttttgata      1920 atctcatgac caaaatccct taacgtgagt tttcgttcca ctgagcgtca gaccccgta       1979
```

<210> SEQ ID NO 34
<211> LENGTH: 2714
<212> TYPE: DNA
<213> ORGANISM: Artificial sequence
<220> FEATURE:
<223> OTHER INFORMATION: Sequence is a de novo synthesized plasmid.

<400> SEQUENCE: 34

```
ccgccgcgcc gcttccactg agcgtcagac cccgtagaaa agatcaaagg atcttcttga       60
gatccttttt ttctgcgcgt aatctgctgc ttgcaaacaa aaaaaccacc gctaccagcg      120
gtggtttgtt tgccggatca agagctacca actctttttc cgaaggtaac tggcttcagc      180
agagcgcaga taccaaatac tgtccttcta gtgtagccgt agttaggcca ccacttcaag      240
aactctgtag caccgcctac atacctcgct ctgctaatcc tgttaccagt ggctgctgcc      300
```

-continued

```
agtggcgata agtcgtgtct taccggggttg gactcaagac gatagttacc ggataaggcg    360
cagcggtcgg gctgaacggg gggttcgtgc acacagccca gcttggagcg aacgacctac    420
accgaactga atacctaca gcgtgagcta tgagaaagcg ccacgcttcc cgaagggaga    480
aaggcggaca ggtatccggt aagcggcagg gtcggaacag gagagcgcac gagggagctt    540 ccaggggggaa acgcctggta tctttatagt cctgtcgggt ttcgccacct ctgacttgag    600
cgtcgatttt tgtgatgctc gtcagggggg cggagcctat ggaaaaacgc cagcaacgcg    660 gccttttttac ggttcctggc cttttgctgg ccttttgctc acatgttctt tcctgcgtta    720 tccctgatt ctgtggataa ccgtattacc gcctttgagt gagctgatac cgctcgccgc    780
agccgaacga ccgagcgcag cgagtcagtg agcgaggaag cggaagagcg cctgatgcgg    840
tattttctcc ttacgcatct gtgcggtatt tcacaccgca tatggtgcac tctcagtaca    900
atctgctctg atgccgcata gttaagccag tatacactcc gctatcgcta cgtgactggg    960
tcatggctgc gccccgacac ccgccaacac ccgctgacgc gccctgacgg gcttgtctgc   1020
tcccggcatc cgcttacaga caagctgtga ccgtctccgg gagctgcatg tgtcagaggt   1080
tttcaccgtc atcaccgaaa cgcgcgaggc agctgcggta aagctcatca gcgtggtcgt   1140
gaagcgattc acagatgtct gcctgttcat ccgcgtccag ctcgttgagt ttctccagaa   1200
gcgttaatgt ctggcttctg ataaagcggg ccatgttaag ggcggttttt tcctgtttgg   1260
tcactgatgc ctccgtgtaa gggggatttc tgttcatggg gtaatgata ccgatgaaac   1320 gagagaggat gctcacgata cgggttactg atgatgaaca tgcccggtta ctggaacgtt   1380
gtgagggtaa acaactggcg gtatggatgc ggcgggacca gagaaaaatc actcagggtc   1440
aatgccagcg cttcgttaat acagatgtag gtgttccaca gggtagccag cagcatcctg   1500
cgatgcagat ccggaacata atggtgcagg cgctgactt ccgcgttggc ggggcgcccg   1560
ggcggcgggc gaagccactg gagcacctca aaaacaccat catacactaa atcagtaagt   1620
tggcagcatc acccgacgca ctttgcgccg aataaatacc tgtgacggaa gatcacttcg   1680
cagaataaat aaatcctggt gtccctgttg ataccgggaa gccctgggcc aacttttggc   1740
gaaaatgaga cgttgatcgg cacgtaagag gttccaactt tcaccataat gaaataagat   1800
cactaccggg cgtattttttt gagttatcga gattttcagg agctaaggaa gctaaaatgg   1860
agaaaaaaat cactggatat accaccgttg atatatccca atggcatcgt aaagaacatt   1920
ttgaggcatt tcagtcagtt gctcaatgta cctataacca gaccgttcag ctggatatta   1980
cggccttttt aaagaccgta aagaaaaata agcacaagtt ttatccggcc tttattcaca   2040
ttcttgcccg cctgatgaat gctcatccgg aattccgtat ggcaatgaaa gacggtgagc   2100
tggtgatatg ggatagtgtt cacccttgtt acaccgtttt ccatgagcaa actgaaacgt   2160
tttcatcgct ctggagtgaa taccacgacg atttccggca gtttctacac atatattcgc   2220
aagatgtggc gtgttacggt gaaaacctgg cctatttccc taaagggttt attgagaata   2280 tgttttttcgt ctcagccaat ccctgggtga gtttcaccag ttttgattta aacgtggcca   2340
atatggacaa cttcttcgcc cccgttttca ccatgggcaa atattatacg caaggcgaca   2400
aggtgctgat gccgctggcg attcaggttc atcatgccgt ctgtgatggc ttccatgtcg   2460
gcagaatgct taatgaatta caacagtact gcgatgagtg gcagggcggg gcgtaatttt   2520
tttaaggcag ttattggtgc ccttaaacgc ctggtgctac gcctgaataa gtgataataa   2580
gcggatgaat ggcagaaatt cgaaagcaaa ttcgacccgg tcgtcggttc agggcagggt   2640
```

```
cgttaaatag ccgcttatgt ctattgctgg tttaccggtt tattgactac cggaagcagt    2700
gtgaccgtgt gctt                                                      2714

<210> SEQ ID NO 35
<211> LENGTH: 2191
<212> TYPE: DNA
<213> ORGANISM: Artificial sequence
<220> FEATURE:
<223> OTHER INFORMATION: Sequence is a de novo synthesized plasmid.

<400> SEQUENCE: 35
ccgccgcgcc gcttccactg agcgtcagac cccttaataa gatgatcttc ttgagatcgt      60
tttggtctgc gcgtaatctc ttgctctgaa aacgaaaaaa ccgccttgca gggcggtttt     120
tcgaaggttc tctgagctac caactctttg aaccgaggta actggcttgg aggagcgcag     180
tcaccaaaac ttgtcctttc agtttagcct taaccggcgc atgacttcaa gactaactcc     240
tctaaatcaa ttaccagtgg ctgctgccag tggtgctttt gcatgtcttt ccgggttgga     300
ctcaagacga tagttaccgg ataaggcgca gcggtcggac tgaacggggg gttcgtgcat     360
acagtccagc ttggagcgaa ctgcctaccc ggaactgagt gtcaggcgtg aatgagaca     420 aacgcggcca taacagcgga tgacaccgg taaaccgaaa ggcaggaaca ggagagcgca     480
cgagggagcc gccaggggga aacgcctggt atctttatag tcctgtcggg tttcgccacc     540
actgatttga gcgtcagatt tcgtgatgct tgtcagggg gcggagccta tggaaaaacg     600
gctttgccgc ggccctctca cttccctgtt aagtatcttc ctggcatctt ccaggaaatc     660
tccgccccgt tcgtaagcca tttccgctcg ccgcagtcga acgaccgagc gtagcgagtc     720
agtgagcgag gaagcggaat atatcctgta tcacatattc tgctgacgca ccggtgcagc     780
cttttttctc ctgccacatg aagcacttca ctgacaccct catcagtgcc aacatagtaa     840
gccagtatac actccgctag cgctgaggtc tgcctcgtga agaaggtgtt gctgactcat     900
accaggcctg aatcgcccca tcatccagcc agaaagtgag ggagccacgg ttgatgagag     960
ctttgttgta ggtggaccag ttggtgattt tgaacttttg ctttgccacg gaacggtctg    1020
cgttggcggg gcgcccgggc ggcgggcgaa gccactggag cacctcaaaa acaccatcat    1080
acactaaatc agtaagttgg cagcatcacc cgacgcactt tgcgccgaat aaatacctgt    1140
gacggaagat cacttcgcag aataaataaa tcctggtgtc cctgttgata ccgggaagcc    1200
ctgggccaac ttttggcgaa aatgagacgt tgatcggcac gtaagaggtt ccaactttca    1260
ccataatgaa ataagatcac taccgggcgt atttttgag ttatcgagat tttcaggagc    1320
taaggaagct aaaatggaga aaaaatcac tggatatacc accgttgata tatcccaatg    1380
gcatcgtaaa gaacattttg aggcatttca gtcagttgct caatgtacct ataaccagac    1440
cgttcagctg gatattacgg cctttttaaa gaccgtaaag aaaaataagc acaagtttta    1500
tccggccttt attcacattc ttgcccgcct gatgaatgct catccggaat tccgtatggc    1560
aatgaaagac ggtgagctgg tgatatggga tagtgttcac ccttgttaca ccgttttcca    1620
tgagcaaact gaaacgtttt catcgctctg gagtgaatac cacgacgatt ccggcagtt    1680 tctacacata tattcgcaag atgtggcgtg ttacggtgaa aacctggcct atttccctaa    1740
agggtttatt gagaatatgt ttttcgtctc agccaatccc tgggtgagtt tcaccagttt    1800
tgatttaaac gtggccaata tggacaactt cttcgccccc gttttcacca tgggcaaata    1860
ttatacgcaa ggcgacaagg tgctgatgcc gctggcgatt caggttcatc atgccgtctg    1920
tgatggcttc catgtcggca gaatgcttaa tgaattacaa cagtactgcg atgagtggca    1980
```

```
gggcggggcg taatttttttt aaggcagtta ttggtgccct aaaacgcctg gtgctacgcc    2040
tgaataagtg ataataagcg gatgaatggc agaaattcga aagcaaattc gacccggtcg    2100
tcggttcagg gcagggtcgt taaatagccg cttatgtcta ttgctggttt accggtttat    2160
tgactaccgg aagcagtgtg accgtgtgct t                                    2191

<210> SEQ ID NO 36
<211> LENGTH: 1992
<212> TYPE: DNA
<213> ORGANISM: Artificial sequence
<220> FEATURE:
<223> OTHER INFORMATION: Sequence is a de novo synthesized plasmid.

<400> SEQUENCE: 36
ccgccgcgcc gcttccactg agcgtcagac cccgtagaaa agatcaaagg atcttcttga      60 gatcctttt  ttctgcgcgt aatctgctgc ttgcaaacaa aaaaaccacc gctaccagcg     120
gtggtttgtt tgccggatca agagctacca actcttttc cgaaggtaac tggcttcagc      180
agagcgcaga taccaaatac tgtccttcta gtgtagccgt agttaggcca ccacttcaag     240
aactctgtag caccgcctac atacctcgct ctgctaatcc tgttaccagt ggctgctgcc     300
agtggcgata gtcgtgtct taccggggtgt gactcaagac gatagttacc ggataaggcg     360
cagcggtcgg gctgaacggg gggttcgtgc acacagccca gcttggagcg aacgacctac     420
accgaactga gatacctaca gcgtgagcta tgagaaagcg ccacgcttcc cgaagggaga     480
aaggcggaca ggtatccggt aagcggcagg gtcggaacag gagagcgcac gagggagctt     540
ccagggggaa acgcctggta tctttatagt cctgtcgggt ttcgccacct ctgacttgag     600
cgtcgatttt tgtgatgctc gtcagggggg cggagcctat ggaaaaacgc cagcaacgcg     660 gccttttttac ggttcctggc cttttgctgg ccttttgctc acatgttctt cctgcgtta    720 tcccctgatt ctgtggataa ccgtattacc gcctttgagt gagctgatac cgctcgccgc     780
agccgaacga ccgagcgcag cgagtcagtg agcgaggaag cggaaggcgg ggcgcccggg     840
cggcgggcga agccactgga gcacctcaaa aacaccatca tacactaaat cagtaagttg     900
gcagcatcac ccgacgcact tgcgccgaa taaatacctg tgacggaaga tcacttcgca     960
gaataaataa atcctggtgt ccctgttgat accgggaagc cctgggccaa cttttggcga    1020
aaatgagacg ttgatcggca cgtaagaggt tccaactttc accataatga aataagatca    1080
ctaccgggcg tatttttga gttatcgaga ttttcaggag ctaaggaagc taaaatggag     1140
aaaaaaatca ctggatatac caccgttgat atatcccaat ggcatcgtaa agaacatttt    1200
gaggcatttc agtcagttgc tcaatgtacc tataaccaga ccgttcagct ggatattacg    1260
gcctttttaa agaccgtaaa gaaaaataag cacaagtttt atccggcctt tattcacatt    1320
cttgcccgcc tgatgaatgc tcatccggaa ttccgtatgg caatgaaaga cggtgagctg    1380
gtgatatggg atagtgttca cccttgttac accgttttcc atgagcaaac tgaaacgttt    1440
tcatcgctct ggagtgaata ccacgacgat ttccggcagt ttctacacat atattcgcaa    1500
gatgtggcgt gttacggtga aaacctggcc tatttcccta aagggtttat tgagaatatg    1560
tttttcgtct cagccaatcc ctgggtgagt ttcaccagtt ttgatttaaa cgtggccaat    1620
atggacaact tcttcgcccc cgttttcacc atgggcaaat attatacgca aggcgacaag    1680
gtgctgatgc cgctggcgat tcaggttcat catgccgtct gtgatggctt ccatgtcggc    1740
agaatgctta atgaattaca acagtactgc gatgagtggc agggcggggc gtaatttttt    1800
```

```
taaggcagtt attggtgccc ttaaacgcct ggtgctacgc ctgaataagt gataataagc    1860
ggatgaatgg cagaaattcg aaagcaaatt cgacccggtc gtcggttcag ggcagggtcg    1920
ttaaatagcc gcttatgtct attgctggtt taccggttta ttgactaccg gaagcagtgt    1980
gaccgtgtgc tt                                                       1992

<210> SEQ ID NO 37
<211> LENGTH: 1906
<212> TYPE: DNA
<213> ORGANISM: Artificial sequence
<220> FEATURE:
<223> OTHER INFORMATION: Sequence is a de novo synthesized plasmid.

<400> SEQUENCE: 37
ccgccgcgcc gcttccactg agcgtcagac cccttaataa gatgatcttc ttgagatcgt      60
tttggtctgc gcgtaatctc ttgctctgaa acgaaaaaa ccgccttgca gggcggtttt     120
tcgaaggttc tctgagctac caactctttg aaccgaggta actggcttgg aggagcgcag    180
tcaccaaaac ttgtcctttc agtttagcct taaccggcgc atgacttcaa gactaactcc    240
tctaaatcaa ttaccagtgg ctgctgccag tggtgctttt gcatgtcttt ccgggttgga    300
ctcaagacga tagttaccgg ataaggcgca gcggtcggac tgaacggggg gttcgtgcat    360
acagtccagc ttggagcgaa ctgcctaccc ggaactgagt gtcaggcgtg aatgagaca     420 aacgcggcca taacagcgga tgacaccgg taaaccgaaa ggcaggaaca ggagagcgca     480
cgagggagcc gccaggggga aacgcctggt atctttatag tcctgtcggg tttcgccacc    540
actgatttga gcgtcagatt tcgtgatgct tgtcaggggg gcggagccta tggaaaaacg    600
gctttgccgc ggccctctca cttccctgtt aagtatcttc ctggcatctt ccaggaaatc    660
tccgccccgt tcgtaagcca tttccgctcg ccgcagtcga acgaccgagc gtagcgagtc    720
agtgagcgag gaagcggaag gcggggcgcc cgggcggcgg gcgaagccac tggagcacct    780
caaaacaccc atcatacact aaatcagtaa gttggcagca tcacccgacg cactttgcgc    840
cgaataaata cctgtgacgg aagatcactt cgcagaataa ataaatcctg gtgtccctgt    900
tgataccggg aagccctggg ccaacttttg gcgaaaatga cgttgatc ggcacgtaag     960 aggttccaac tttcaccata atgaaataag atcactaccg ggcgtatttt ttgagttatc   1020
gagattttca ggagctaagg aagctaaaat ggagaaaaaa atcactggat ataccaccgt    1080
tgatatatcc caatggcatc gtaaagaaca ttttgaggca tttcagtcag ttgctcaatg    1140
tacctataac cagaccgttc agctggatat tacggccttt ttaaagaccg taaagaaaaa    1200
taagcacaag ttttatccgg cctttattca cattcttgcc cgcctgatga atgctcatcc    1260
ggaattccgt atggcaatga agacggtga gctggtgata tgggatagtg ttcacccttg    1320
ttacaccgtt ttccatgagc aaactgaaac gttttcatcg ctctggagtg aataccacga    1380
cgatttccgg cagtttctac acatatattc gcaagatgtg gcgtgttacg gtgaaaacct    1440
ggcctatttc cctaaagggt ttattgagaa tatgttttc gtctcagcca tccctgggt     1500 gagtttcacc agttttgatt taaacgtggc caatatggac aacttcttcg ccccgttt     1560 caccatgggc aaatattata cgcaaggcga aggtgctg atgccgctgg cgattcaggt    1620
tcatcatgcc gtctgtgatg gcttccatgt cggcagaatg cttaatgaat acaacagta    1680 ctgcgatgag tggcagggcg gggcgtaatt tttttaaggc agttattggt gcccttaaac    1740
gcctggtgct acgcctgaat aagtgataat aagcggatga atggcagaaa ttcgaaagca    1800
aattcgaccc ggtcgtcggt tcagggcagg gtcgttaaat agccgcttat gtctattgct    1860
```
ggtttaccgg tttattgact accggaagca gtgtgaccgt gtgctt        1906

<210> SEQ ID NO 38
<211> LENGTH: 2600
<212> TYPE: DNA
<213> ORGANISM: Artificial sequence
<220> FEATURE:
<223> OTHER INFORMATION: Sequence is a de novo synthesized plasmid.

<400> SEQUENCE: 38
ccgccgcgcc gcttccactg agcgtcagac cccttaataa gatgatcttc ttgagatcgt        60
tttggtctgc gcgtaatctc ttgctctgaa acgaaaaaa ccgccttgca gggcggtttt       120
tcgaaggttc tctgagctac caactctttg aaccgaggta actggcttgg aggagcgcag       180
tcaccaaaac ttgtcctttc agtttagcct taaccggcgc atgacttcaa gactaactcc       240
tctaaatcaa ttaccagtgg ctgctgccag tggtgctttt gcatgtcttt ccgggttgga       300
ctcaagacga tagttaccgg ataaggcgca gcggtcggac tgaacggggg gttcgtgcat       360
acagtccagc ttggagcgaa ctgcctaccc ggaactgagt gtcaggcgtg gaatgagaca       420
aacgcggcca taacagcgga atgacaccgg taaaccgaaa ggcaggaaca ggagagcgca       480
cgagggagcc gccaggggga aacgcctggt atctttatag tcctgtcggg tttcgccacc       540
actgatttga gcgtcagatt tcgtgatgct tgtcaggggg gcggagccta tggaaaaacg       600
gctttgccgc ggccctctca cttccctgtt aagtatcttc ctggcatctt ccaggaaatc       660
tccgccccgt tcgtaagcca tttccgctcg ccgcagtcga acgaccgagc gtagcgagtc       720
agtgagcgag gaagcggaat atatcctgta tcacatattc tgctgacgca ccggtgcagc       780
cttttttctc ctgccacatg aagcacttca ctgacaccct catcagtgcc aacatagtaa       840
gccagtatac actccgctag cgctgaggtc tgcctcgtga agaaggtgtt gctgactcat       900
accaggcctg aatcgcccca tcatccagcc agaaagtgag ggagccacgg ttgatgagag       960
ctttgttgta ggtggaccag ttggtgattt tgaacttttg ctttgccacg gaacggtctg      1020
cgttggcggg gcgcccgggc ggcgggcgtt ctcatgtttg acagcttatc atcgataagc      1080
tttaatgcgg tagtttatca cagttaaatt gctaacgcag tcaggcaccg tgtatgaaat      1140
ctaacaatgc gctcatcgtc atcctcggca ccgtcaccct ggatgctgta ggcataggct      1200
tggttatgcc ggtactgccg ggcctcttgc gggatatcgt ccattccgac agcatcgcca      1260
gtcactatgg cgtgctgcta gcgctatatg cgttgatgca atttctatgc gcacccgttc      1320
tcggagcact gtccgaccgc tttggccgcc gcccagtcct gctcgcttcg ctacttggag      1380
ccactatcga ctacgcgatc atggcgacca cacccgtcct gtggatcctc tacgccggac      1440
gcatcgtggc cggcatcacc ggcgccacag gtgcggttgc tggcgcctat atcgccgaca      1500
tcaccgatgg ggaagatcgg gctcgccact tcgggctcat gagcgcttgt ttcggcgtgg      1560
gtatggtggc aggccccgtg gccgggggac tgttgggcgc catctccttg catgcaccat      1620
tccttgcggc ggcggtgctc aacggcctca acctactact gggctgcttc ctaatgcagg      1680
agtcgcataa gggagagcgt cgaccgatgc ccttgagagc cttcaaccca gtcagctcct      1740
tccggtgggc gcggggcatg actatcgtcg ccgcacttat gactgtcttc tttatcatgc      1800
aactcgtagg acaggtgccg gcagcgctct gggtcatttt cggcgaggac cgctttcgct      1860
ggagcgcgac gatgatcggc ctgtcgcttg cggtattcgg aatcttgcac gccctcgctc      1920
aagccttcgt cactggtccc gccaccaaac gtttcggcga agcaggcc attatcgccg      1980

```
gcatggcggc cgacgcgctg ggctacgtct tgctggcgtt cgcgacgcga ggctggatgg   2040
ccttccccat tatgattctt ctcgcttccg gcggcatcgg gatgcccgcg ttgcaggcca   2100
tgctgtccag gcaggtagat gacgaccatc agggacagct tcaaggatcg ctcgcggctc   2160
ttaccagcct aacttcgatc actggaccgc tgatcgtcac ggcgatttat gccgcctcgg   2220
cgagcacatg gaacggttg gcatggattg taggcgccgc cctataccttt gtctgcctcc   2280 ccgcgttgcg tcgcggtgca tggagccggg ccacctcgac ctgaatggaa gccggcggca   2340
cctcgctaac ggattcacca ctccaagaat tggagccaat caattcttgc ggagaactgt   2400
gaatgcgcaa accaaccctt ggcagaacat atccatcgcg tccgccatct ccagcagccg   2460
cacgcggcgc atctcgggca gcgttgggtc ctggccacgg gtgcgcatga tcgtgctcct   2520
gtcgttgagg acccggctag gctggcgggg ttgccttact ggttagcaga atgaatcacc   2580
gatacgcgag cgaacgtgaa                                               2600

<210> SEQ ID NO 39
<211> LENGTH: 2315
<212> TYPE: DNA
<213> ORGANISM: Artificial sequence
<220> FEATURE:
<223> OTHER INFORMATION: Sequence is a de novo synthesized plasmid.

<400> SEQUENCE: 39
ccgccgcgcc gcttccactg agcgtcagac cccttaataa gatgatcttc ttgagatcgt     60
tttggtctgc gcgtaatctc ttgctctgaa acgaaaaaa ccgccttgca gggcggtttt    120
tcgaaggttc tctgagctac caactctttg aaccgaggta actggcttgg aggagcgcag    180
tcaccaaaac ttgtcctttc agtttagcct taaccggcgc atgacttcaa gactaactcc    240
tctaaatcaa ttaccagtgg ctgctgccag tggtgctttt gcatgtcttt ccgggttgga    300
ctcaagacga tagttaccgg ataaggcgca gcggtcggac tgaacggggg gttcgtgcat    360
acagtccagc ttggagcgaa ctgcctaccc ggaactgagt gtcaggcgtg aatgagaca    420 aacgcggcca taacagcgga atgacaccgg taaaccgaaa gcaggaaca ggagagcgca    480 cgagggagcc gccaggggga aacgcctggt atctttatag tcctgtcggg tttcgccacc    540
actgatttga gcgtcagatt tcgtgatgct tgtcaggggg gcggagccta tggaaaaacg    600
gctttgccgc ggccctctca cttccctgtt aagtatcttc ctggcatctt ccaggaaatc    660
tccgccccgt tcgtaagcca tttccgctcg ccgcagtcga acgaccgagc gtagcgagtc    720
agtgagcgag gaagcggaag gcggggcgcc cgggcggcgg gcgttctcat gtttgacagc    780
ttatcatcga taagctttaa tgcggtagtt tatcacagtt aaattgctaa cgcagtcagg    840
caccgtgtat gaaatctaac aatgcgctca tcgtcatcct cggcaccgtc accctggatg    900
ctgtaggcat aggcttggtt atgccggtac tgccgggcct cttgcgggat atcgtccatt    960
ccgacagcat cgccagtcac tatggcgtgc tgctagcgct atatgcgttg atgcaatttc   1020
tatgcgcacc cgttctcgga gcactgtccg accgctttgg ccgccgccca gtcctgctcg   1080
cttcgctact tggagccact atcgactacg cgatcatggc gaccacaccc gtcctgtgga   1140
tcctctacgc cggacgcatc gtggccggca tcaccggcgc cacaggtgcg gttgctggcg   1200
cctatatcgc cgacatcacc gatggggaag atcgggctcg ccacttcggg ctcatgagcg   1260
cttgtttcgg cgtgggtatg gtggcaggcc ccgtggccgg gggactgttg ggcgccatct   1320
ccttgcatgc accattcctt gcggcggcgg tgctcaacgg cctcaaccta ctactgggct   1380
gcttcctaat gcaggagtcg cataagggag agcgtcgacc gatgcccttg agagccttca   1440
```

```
acccagtcag ctccttccgg tgggcgcggg gcatgactat cgtcgccgca cttatgactg    1500
tcttctttat catgcaactc gtaggacagg tgccggcagc gctctgggtc attttcggcg    1560
aggaccgctt tcgctggagc gcgacgatga tcggcctgtc gcttgcgta ttcggaatct     1620 tgcacgccct cgctcaagcc ttcgtcactg gtcccgccac caaacgtttc ggcgagaagc    1680
aggccattat cgccggcatg gcggccgacg cgctgggcta cgtcttgctg gcgttcgcga    1740
cgcgaggctg gatggccttc cccattatga ttcttctcgc ttccggcggc atcgggatgc    1800
ccgcgttgca ggccatgctg tccaggcagg tagatgacga ccatcaggga cagcttcaag    1860
gatcgctcgc ggctcttacc agcctaactt cgatcactgg accgctgatc gtcacggcga    1920
tttatgccgc ctcggcgagc acatggaacg ggttggcatg gattgtaggc gccgccctat    1980
accttgtctg cctccccgcg ttgcgtcgcg gtgcatggag ccgggccacc tcgacctgaa    2040
tggaagccgg cggcacctcg ctaacggatt caccactcca agaattggag ccaatcaatt    2100
cttgcggaga actgtgaatg cgcaaaccaa cccttggcag aacatatcca tcgcgtccgc    2160
catctccagc agccgcacgc ggcgcatctc gggcagcgtt gggtcctggc acgggtgcg    2220 catgatcgtg ctcctgtcgt tgaggacccg gctaggctgg cggggttgcc ttactggtta    2280
gcagaatgaa tcaccgatac gcgagcgaac gtgaa                              2315
```

<210> SEQ ID NO 40
<211> LENGTH: 2267
<212> TYPE: DNA
<213> ORGANISM: Artificial sequence
<220> FEATURE:
<223> OTHER INFORMATION: Sequence is a de novo synthesized plasmid.

<400> SEQUENCE: 40

```
ccgccgcgcc gcttccactg agcgtcagac cccttaataa gatgatcttc ttgagatcgt      60
tttggtctgc gcgtaatctc ttgctctgaa acgaaaaaa ccgccttgca gggcggtttt     120
tcgaaggttc tctgagctac caactctttg aaccgaggta actggcttgg aggagcgcag    180
tcaccaaaac ttgtcctttc agtttagcct taaccgcgc atgacttcaa gactaactcc     240
tctaaatcaa ttaccagtgg ctgctgccag tggtgctttt gcatgtcttt ccgggttgga    300
ctcaagacga tagttaccgg ataaggcgca gcggtcggac tgaacggggg gttcgtgcat    360
acagtccagc ttggagcgaa ctgcctaccc ggaactgagt gtcaggcgtg aatgagaca    420 aacgcggcca taacagcgga tgacaccgg taaaccgaaa ggcaggaaca ggagagcgca    480
cgagggagcc gccaggggga aacgcctggt atctttatag tcctgtcggg tttcgccacc    540
actgatttga gcgtcagatt tcgtgatgct tgtcaggggg gcggagccta tggaaaaacg    600
gctttgccgc ggccctctca cttccctgtt aagtatcttc ctggcatctt ccaggaaatc    660
tccgccccgt tcgtaagcca tttccgctcg ccgcagtcga acgaccgagc gtagcgagtc    720
agtgagcgag gaagcggaat atatcctgta tcacatattc tgctgacgca ccggtgcagc    780 ctttttctc ctgccacatg aagcacttca ctgacaccct catcagtgcc aacatagtaa    840
gccagtatac actccgctag cgctgaggtc tgcctcgtga agaaggtgtt gctgactcat    900
accaggcctg aatcgcccca tcatccagcc agaaagtgag ggagccacgg ttgatgagag    960
ctttgttgta ggtggaccag ttggtgattt tgaactttg ctttgccacg gaacggtctg   1020
cgttggcggg gcgcccggc ggcggcgtt gtcgggaaga tgcgtgatct gatccttcaa    1080
ctcagcaaaa gttcgattta ttcaacaaag ccacgttgtg tctcaaaatc tctgatgtta    1140
```

| | |
|---|---|
| cattgcacaa gataaaaata tatcatcatg aacaataaaa ctgtctgctt acataaacag | 1200 |
| taatacaagg ggtgttatga gccatattca acgggaaacg tcttgctcga ggccgcgatt | 1260 |
| aaattccaac atggatgctg atttatatgg gtataaatgg gctcgcgata atgtcgggca | 1320 |
| atcaggtgcg acaatctatc gattgtatgg gaagcccgat gcgccagagt tgtttctgaa | 1380 |
| acatggcaaa ggtagcgttg ccaatgatgt tacagatgag atggtcagac taaactggct | 1440 |
| gacggaattt atgcctcttc cgaccatcaa gcatttatc cgtactcctg atgatgcatg | 1500 |
| gttactcacc actgcgatcc ccgggaaaac agcattccag gtattagaag aatatcctga | 1560 |
| ttcaggtgaa aatattgttg atgcgctggc agtgttcctg cgccggttgc attcgattcc | 1620 |
| tgtttgtaat tgtcctttta acagcgatcg cgtatttcgt ctcgctcagg cgcaatcacg | 1680 |
| aatgaataac ggtttggttg atgcgagtga ttttgatgac gagcgtaatg gctggcctgt | 1740 |
| tgaacaagtc tggaaagaaa tgcataagct tttgccattc tcaccggatt cagtcgtcac | 1800 |
| tcatggtgat ttctcacttg ataaccttat ttttgacgag gggaaattaa taggttgtat | 1860 |
| tgatgttgga cgagtcggaa tcgcagaccg ataccaggat cttgccatcc tatggaactg | 1920 |
| cctcggtgag ttttctcctt cattacagaa acggcttttt caaaaatatg gtattgataa | 1980 |
| tcctgatatg aataaattgc agtttcattt gatgctcgat gagttttct aatcagaatt | 2040 |
| ggttaattgg ttgtaacact ggcagagcat tacgctgact tgacgggacg gcggctttgt | 2100 |
| tgaataaatc gaacttttgc tgagttgaag gatcagatca cgcatcttcc cgacaacgca | 2160 |
| gaccgttccg tggcaaagca aaagttcaaa atcaccaact ggtccaccta caacaaagct | 2220 |
| ctcatcaacc gtggctccct cactttctgg ctggatgatg gggcgat | 2267 |

<210> SEQ ID NO 41
<211> LENGTH: 1982
<212> TYPE: DNA
<213> ORGANISM: Artificial sequence
<220> FEATURE:
<223> OTHER INFORMATION: Sequence is a de novo synthesized plasmid.

<400> SEQUENCE: 41

| | |
|---|---|
| ccgccgcgcc gcttccactg agcgtcagac cccttaataa gatgatcttc ttgagatcgt | 60 |
| tttggtctgc gcgtaatctc ttgctctgaa aacgaaaaaa ccgccttgca gggcggtttt | 120 |
| tcgaaggttc tctgagctac caactctttg aaccgaggta actggcttgg aggagcgcag | 180 |
| tcaccaaaac ttgtcctttc agtttagcct taaccggcgc atgacttcaa gactaactcc | 240 |
| tctaaatcaa ttaccagtgg ctgctgccag tggtgctttt gcatgtcttt ccgggttgga | 300 |
| ctcaagacga tagttaccgg ataaggcgca gcggtcggac tgaacggggg gttcgtgcat | 360 |
| acagtccagc ttggagcgaa ctgcctaccc ggaactgagt gtcaggcgtg aatgagaca | 420 |
| aacgcggcca taacagcgga atgacaccgg taaaccgaaa ggcaggaaca ggagagcgca | 480 |
| cgagggagcc gccaggggga aacgcctggt atctttatag tcctgtcggg tttcgccacc | 540 |
| actgatttga gcgtcagatt tcgtgatgct tgtcaggggg gcggagccta tggaaaaacg | 600 |
| gctttgccgc ggccctctca cttccctgtt aagtatcttc ctggcatctt ccaggaaatc | 660 |
| tccgccccgt tcgtaagcca tttccgctcg ccgcagtcga acgaccgagc gtagcgagtc | 720 |
| agtgagcgag gaagcggaag gcgggcgccc gggcggcgg gcgttgtcgg gaagatgcgt | 780 |
| gatctgatcc ttcaactcag caaaagttcg atttattcaa caaagccacg ttgtgtctca | 840 |
| aaatctctga tgttacattg cacaagataa aaatatatca tcatgaacaa taaaactgtc | 900 |
| tgcttacata aacagtaata caaggggtgt tatgagccat attcaacggg aaacgtcttg | 960 |

```
ctcgaggccg cgattaaatt ccaacatgga tgctgattta tatgggtata aatgggctcg    1020
cgataatgtc gggcaatcag gtgcgacaat ctatcgattg tatgggaagc ccgatgcgcc    1080
agagttgttt ctgaaacatg gcaaaggtag cgttgccaat gatgttacag atgagatggt    1140
cagactaaac tggctgacgg aatttatgcc tcttccgacc atcaagcatt ttatccgtac    1200
tcctgatgat gcatggttac tcaccactgc gatccccggg aaaacagcat tccaggtatt    1260
agaagaatat cctgattcag gtgaaaatat tgttgatgcg ctggcagtgt tcctgcgccg    1320
gttgcattcg attcctgttt gtaattgtcc ttttaacagc gatcgcgtat ttcgtctcgc    1380
tcaggcgcaa tcacgaatga ataacggttt ggttgatgcg agtgattttg atgacgagcg    1440
taatggctgg cctgttgaac aagtctggaa agaaatgcat aagcttttgc cattctcacc    1500
ggattcagtc gtcactcatg gtgatttctc acttgataac cttattttg acgaggggaa     1560 attaataggt tgtattgatg ttggacgagt cggaatcgca gaccgatacc aggatcttgc    1620
catcctatgg aactgcctcg gtgagttttc tccttcatta cagaaacggc ttttcaaaa     1680 atatggtatt gataatcctg atatgaataa attgcagttt catttgatgc tcgatgagtt    1740
tttctaatca gaattggtta attggttgta acactggcag agcattacgc tgacttgacg    1800
ggacggcggc tttgttgaat aaatcgaact tttgctgagt tgaaggatca gatcacgcat    1860
cttcccgaca acgcagaccg ttccgtggca aagcaaaagt tcaaaatcac caactggtcc    1920
acctacaaca aagctctcat caaccgtggc tccctcactt tctggctgga tgatggggcg    1980
at                                                                   1982
```

DE NOVO SYNTHESIZED PLASMID, METHODS OF MAKING AND USE THEREOF

CROSS-REFERENCE TO RELATED APPLICATIONS

Not applicable

STATEMENT REGARDING FEDERALLY SPONSORED RESEARCH OR DEVELOPMENT

Not applicable

REFERENCE TO SEQUENCE LISTING

A sequence listing of this invention is submitted on paper after the Declaration. The sequence listing was generated by software Patent-In 3.1.

BACKGROUND OF THE INVENTION

This invention relates to recombinant DNA technology for making and using a novel plasmid. More particularly it relates to methods for making and using a de novo synthesized plasmid with defined copy number and selection marker. This de novo synthesized plasmid is useful in making other plasmids and cell strains containing these plasmids. Plasmids are extrachromosomal circular double stranded DNA loops that are transferable from one bacterium to another. Plasmids replicate independently of that of the chromosomal DNA of a host cell. The number of plasmid in a host cell is called the copy number of the plasmid. A given plasmid may be present in a low copy number or a high copy number inside a bacterial cell. The copy number is a genetic characteristic of the replication origin of each plasmid. The replication origin of a plasmid determines its copy number.

The type of replication origin divides plasmids into different incompatibility groups. Different plasmids of same incompatibility group cannot stably coexist in one bacterial cell. On the other hand, plasmids of different incompatibility groups can stably coexist in one bacterial cell. For example, different plasmids of the ColE1-type replication origin (such as plasmids of the family's pBR, pUC and the like) cannot coexist stably in one bacterial cell. Different plasmids of p15A-type replication origin (such as plasmids of the family pACYC and the like) cannot coexist stably in one bacterial cell. However a plasmid of the ColE1-type replication origin and a plasmid of p15A-type origin can coexist stably in one bacterial cell because they belong to different incompatibility groups.

In addition to replication origin, plasmids often contain selection marker genes. A selection marker gene normally allows for phenotypic selection in transformed host cells. Some selection marker genes encode proteins conferring host cell resistance to certain antibiotics. Examples of antibiotics resisted by proteins encoded by selection marker genes include ampicillin, tetracycline, chloramphenicol, kanamycin, gentamycin, rifampicin, spectinomycin, streptomycin, and the like.

Plasmids are useful in DNA cloning, DNA amplification, gene expression, gene therapy, DNA immunization, and like biomedical applications. Substantial efforts have been made to construct numerous plasmids. All of the plasmids made from prior arts are modifications of the plasmids previously obtained from natural sources or recombinant sources. These plasmids inevitably contain some DNA sequences with unknown and/or undesirable function (junk sequences). These junk sequences consume cellular resources and contribute to cellular energy drains. In some cases, the junk sequences have detrimental effects on the plasmid applications. Therefore a novel plasmid, which contains relevant sequences, is generated from de novo synthesis and minimizes the junk sequences, will be valuable in the biomedical applications.

SUMMARY OF THE INVENTION

In general, the present invention provides a novel plasmid. More specifically, the invention provides a de novo synthesized plasmid comprising at least a replication origin and a selection marker gene wherein (a) the replication origin contains sequences relevant to autonomous plasmid replication in a host cell; and
(b) the selection marker gene contains sequences relevant to the selection of the plasmid in a host cell.

Wherein the de novo synthesized plasmid is not modified from the plasmid previously obtained from natural or recombinant sources. Wherein the replication origin allows the autonomous plasmid replication in a host cell. Wherein the selection marker gene encodes a product indicative of plasmid maintenance in a host cell.

The present invention further provides a method of preparing the de novo synthesized plasmid combined from at least two DNA fragments comprising:

(a) preparing a linear replication origin DNA fragment;
(b) preparing a linear selection marker gene DNA fragment;
(c) combining the DNA fragments prepared from steps (a) and (b) to form a circular de novo synthesized plasmid;
(d) introducing the plasmid made from step (c) into a host cell; and
(e) selecting the plasmid with appropriate replication origin and selection marker from transformed host cells.

Wherein any DNA fragment alone used for combining the de novo synthesized plasmid cannot confer both autonomous DNA replication and selection to a plasmid. In one preferred embodiment, the linear DNA fragment is prepared from polymerase chain reaction (PCR). In another preferred embodiment, the linear DNA fragment is prepared from restriction digestion.

The present invention also provides a method of using the de novo synthesized plasmid comprising:

(a) linearizing the de novo synthesized plasmid;
(b) inserting one or more functional DNA fragments into the plasmid to make other plasmids;
(c) introducing the plasmids made from step (b) into host cells;
(d) selecting the plasmids and the host cells with desired properties; and
(e) using the plasmids and the host cells for biomedical applications Wherein the de novo synthesized plasmid is linearized by restriction digestion. Wherein the de novo synthesized plasmid is linearized by PCR. Wherein the functional DNA fragments encode a promoter, a regulatory sequence, a ribosome binding site, restriction sites, a terminator, a polypeptide, a replication origin, a selection marker gene, and the like useful DNA sequences. Wherein the desired properties are plasmid replication, selection, and other properties added by functional DNA fragments inserted from step (b). Wherein the biomedical applications are DNA cloning, DNA amplification, gene expression, gene therapy, DNA immunization, and the like.

Further objects and advantages of the invention will become apparent from a consideration of the drawings and ensuing description.

BRIEF DESCRIPTION OF THE FIGURES

FIG. 4. Protein expression studies. Experimental results show expression of proteins by plasmids generated from de novo synthesized plasmids p4TI3E and p2CXL.

DETAILED DESCRIPTION OF THE INVENTION

Figure 1:
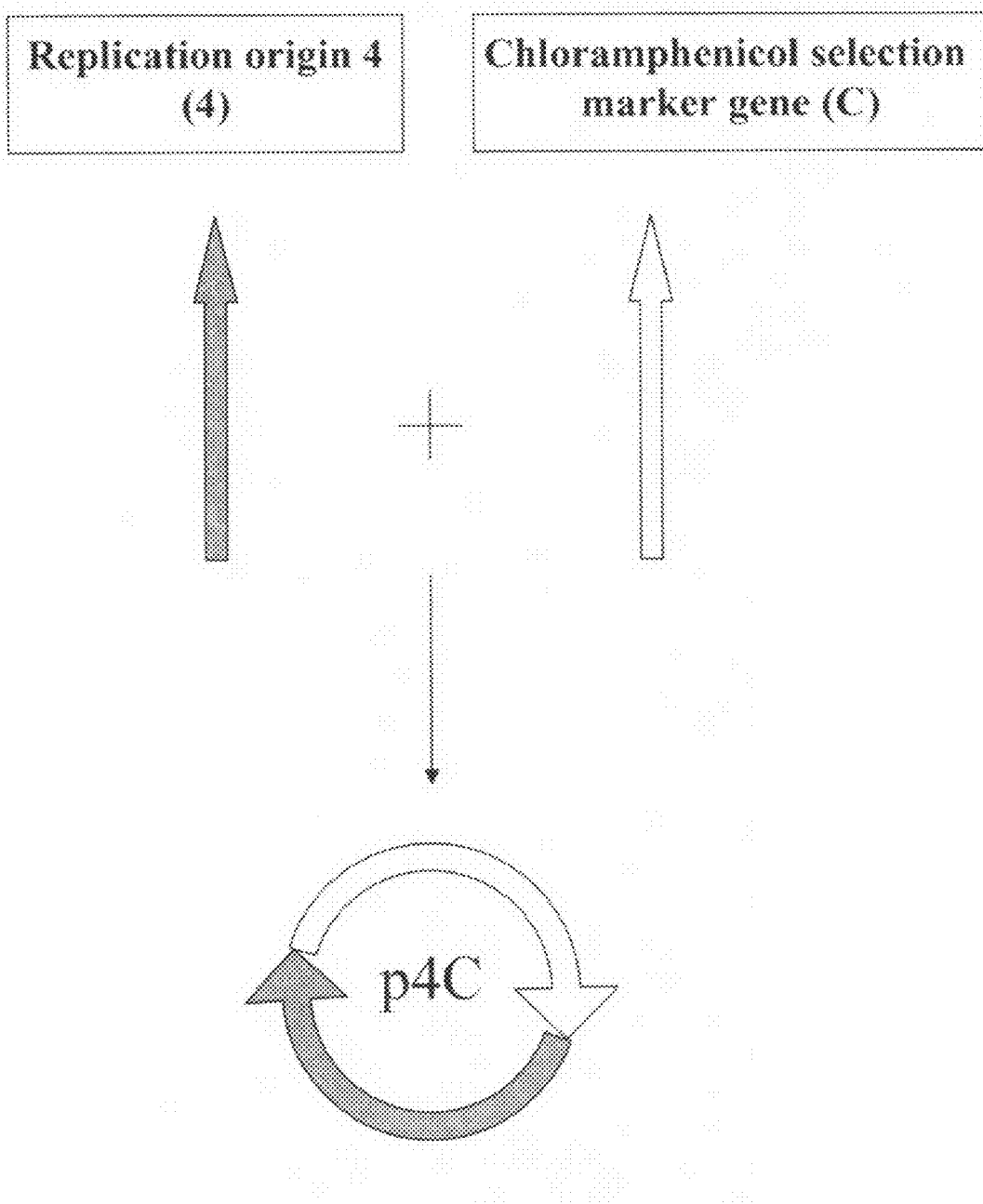
FIG. 1. Schematic diagrams of construction of a de novo synthesized plasmid p4T. The arrow indicates the direction of transcription.

The invention relates to a novel recombinant plasmid.

In one embodiment, the invention relates to a de novo synthesized plasmid comprising at least a combination of a replication origin and a selection marker gene wherein (a) the replication origin contains sequences relevant to autonomous plasmid replication in a host cell. In one preferred embodiment, the sequences relevant for autonomous plasmid replication are determined by prior art publications. In another preferred embodiment, the sequences relevant for autonomous plasmid replication are determined by experiments. In a preferred embodiment, the replication origin allows the plasmid to replicate in a low copy number in a host cell (less than 20 copies per cell). In another preferred embodiment, the replication origin allows the plasmid replication in a high copy number in a host cell (more than 200 copies per cell). In a further preferred embodiment, the replication origin allows the plasmid to replicate in an intermediate copy number in a host cell (from 20 to 200 copies per cell). In one preferred embodiment, the replication origin is from ColE1-type incompatibility group. In another preferred embodiment, it is from p15A-type incompatibility group. One skilled in the art will recognize that they can be from other types of origins as long as they allow autonomous plasmid replication in a host cell. For example, they can be from M13, pSC101, R6-5-type origins and the like; and (b) the selection marker gene contains sequences relevant for allowing the selection of the plasmid in a host cell. In one preferred embodiment, the sequences relevant for allowing the selection of the plasmid are determined by prior art publications. In another preferred embodiment, the sequences relevant for allowing the selection of the plasmid are determined by experiments. The selection marker gene normally allows for phenotypic selection of the plasmid in a transformed host cells. The selection marker gene often encodes a product indicative of plasmid maintenance in a host cell. Some selection marker genes are antibiotic resistance genes. In one preferred embodiment, the selection marker gene is ampicillin resistance gene. In another preferred embodiment, the selection marker gene is chloramphenicol resistance gene. In a further preferred embodiment, the selection marker gene is tetracycline resistance gene. In yet another preferred embodiment, the selection marker gene is kanamycin resistance gene. The selection marker gene contains a promoter, a ribosome binding site, a open reading frame encoding a protein product, a terminator and the like sequences necessary for allowing the selection of a host cell.

Wherein the de novo synthesized plasmid is not modified from the plasmid previously obtained from natural or recombinant sources.

The type of replication origin determines the compatibility of plasmids in a host cell. In applications such as protein co-expression, compatible plasmids from different replication origins of different compatibility groups are needed. The type of replication origin also determines the copy number of a plasmid. Within an incompatibility group, the copy number of a plasmid can be different. For example, pBR322 gives low copy number and pUC19 produces high copy number while they all belong to ColE1 incompatibility group. High copy number is advantageous for applications such as plasmid amplification and protein expression. However high copy number also depletes cellular resources and contributes cellular energy drain. Toxic DNA fragments are often difficult to be cloned and established in a high copy number plasmids. In some cases, proteins are expressed at a higher level in low copy number plasmids. Therefore low copy number plasmids are also needed. In one preferred embodiment, high copy number plasmids are selected. In another preferred embodiment, low copy number plasmids are selected. In a further preferred embodiment, the intermediate copy number plasmids are selected. The copy number of a plasmid can be estimated after the plasmid prep.

In one preferred embodiment, the de novo synthesized plasmid comprises of a replication origin with a selection marker gene. In another preferred embodiment, the de novo synthesized plasmid comprises of another replication origin with another selection marker gene. In further preferred embodiment, the de novo synthesized plasmid comprises of a further different replication origin and a further different selection marker gene. These replication origins may be from same incompatibility group and with different copy numbers. They may also be from different incompatibility groups and with different copy numbers. These selection marker genes may be any genes that allow phenotypic selection of the plasmids in host cells. As will be understood by those of skill in the art that the replication origin and selection marker gene used to form the de novo synthesized plasmid can comprise of any combination.

In another preferred embodiment, the invention relates to a method of preparing a de novo synthesized plasmid combined from at least two DNA fragments comprising:

(a) preparing a linear replication origin DNA fragment;
(b) preparing a linear selection marker gene DNA fragment;
(c) combining the DNA fragments prepared in steps (a) and (b) to form a circular de novo synthesized plasmid;
(d) introducing the de novo synthesized plasmid made from step (c) into host cells; and
(e) selecting the plasmid with appropriate replication origin and selection marker from transformed host cells.

Wherein the linear replication origin DNA fragment contains sequences relevant to autonomous DNA replication. Wherein the linear selection marker gene DNA fragment contains sequences relevant to phenotypic selection of a plasmid in a host cell. Wherein any DNA fragment alone used for combining de novo synthesized plasmid cannot confer both autonomous DNA replication and selection to a plasmid. To minimize the cellular energy drain, the sequences with unknown and undesirable functions are minimized in these DNA fragments. The DNA fragments containing the replication origin or selection marker gene may be prepared from restriction digested DNA or PCR reaction.

Wherein the replication origin and selection marker gene are combined together with or without linker DNA sequences. Linker DNA sequences are short DNA sequences necessary to link two or more DNA fragments together. In one preferred embodiment, the replication origin and selection marker gene are combined together by linker sequences designed for exonuclease-mediated cloning. In another preferred embodiment, the replication origin and selection marker gene are combined together by linker sequences designed for restriction enzyme-mediated cloning. In a further preferred embodiment, the replication origin and selection marker gene are combined together without any linker sequences by blunt end ligation. In yet another preferred embodiment, the replication origin and selection marker gene are combined together without any linker sequences by exonuclease-mediated cloning. In this case, homologous sequences are designed at the ends of the linear DNA fragments by synthetic oligos that the DNA fragments obtained by PCR with these oligos may anneal together after exonuclease treatment.

The linker DNA sequences are located between the replication origin and the selection marker gene. To minimize the cellular energy drain, the linker sequences should be as short as possible. The length of the linker sequences is the length necessary for efficient cloning. Depends on the particular method used to combine the DNA fragments, the length of linker sequences will vary. In one preferred embodiment, the length of linker sequences is 24 nucleotides. In another preferred embodiment, the length of linker sequences is 12 nucleotides. In yet another preferred embodiment, the length of linker sequences is at least the length of a restriction enzyme recognition site. In a further preferred embodiment, no linker is used for blunt end ligation. One skilled in the art would recognize that the linker length would be what it is needed to link the DNA fragments together.

It is convenient for the de novo synthesized plasmid to contain at least one restriction site. The restriction site will be used to linearize the plasmid, therefore it should be unique for the plasmid. When no convenient restriction site is available, the plasmid may be linearized by PCR. When blunt end ligation is used, the DNA sequences can be designed that the ligated DNA may create a unique restriction site. In the case that the DNA fragments used to make these de novo synthesized plasmids contains restriction sites designed for plasmid linearization, these restriction sites may be mutated to make the linearization restriction site unique.

Wherein the combination of these DNA fragments can be achieved by annealing sequences produced by an exonuclease treatment. In one preferred embodiment, the sequences are produced by exonuclease III. In another preferred embodiment, the sequences are produced by lambda exonuclease. In a further preferred embodiment, the sequences are produced by an exonuclease activity of a DNA polymerase such as T4 DNA polymerase and the like. The annealing sequences can also be produced by restriction enzyme digestion. Wherein the combination of these DNA fragments can also be achieved by blunt end ligation.

The selection of the circular plasmids is achieved by adding an agent to the growth medium. The agent is usually an antibiotic. In one preferred embodiment, the antibiotic is ampicillin. In another preferred embodiment, the antibiotic is chloramphenicol. In a further preferred embodiment, the antibiotic is tetracycline. In yet another preferred embodiment, the antibiotic is kanamycin.

In a further preferred embodiment, the present invention also relates a method of using the de novo synthesized plasmid:

(a) linearizing the de novo synthesized plasmid;
(b) inserting one or more functional DNA fragments into the linearized plasmid to make other plasmids;
(c) introducing the plasmids made from step (b) into host cells;
(d) selecting the plasmids and host cells with desired properties; and
(e) using the plasmids and host cells for biomedical applications.

Wherein the de novo synthesized plasmid is linearized by restriction digestion. Wherein the de novo synthesized plasmid is linearized by PCR. Wherein the functional DNA fragments encode a promoter, a regulatory sequence, a ribosome binding site, restriction sites, a terminator, a polypeptide, a replication origin, a selection marker gene, and the like useful DNA sequences. To minimize the cellular energy drain, the sequences with unknown and undesirable functions are minimized in these DNA fragments. Wherein the desired properties are plasmid replication, selection, and other properties added by functional DNA fragments inserted from step (b). Wherein the biomedical applications are DNA cloning, DNA amplification, gene expression, gene therapy, DNA immunization, and the like.

A promoter is the DNA sequences where RNA polymerase binds. Promoters can be from prokaryote or eukaryote origin depends on the application of particular plasmid. Examples of the promoters include ara, lac, T7, tac, and trp from prokaryote, AOX1, GAL1, and TEF1 from yeast, MT, PH, and P10 from insect, CMV, RSV, and tk from eukaryotic cells.

A regulatory sequence allows regulated transcription of a gene. It often located immediately upstream or downstream of a promoter. A regulatory sequence often allows a transcription to be regulated by a highly selective chemical or by temperature changes. For example, the regulatory sequence for lac operator allows transcription by adding lactose or isopropy-beta-D-thiogalactopyronoside (IPTG).

A ribosome binding site is also known as the Shine-Dalgarno (SD) sequence. It binds to ribosome allowing translation initiation. Following ribosome binding site is the translation initiation codon ATG. Multiple restriction sites, which are unique to the plasmid, permit insertion of an exogenous gene and verification of plasmid construction. An open reading frame of a polypeptide is placed between the translation initiation codon ATG and translation termination codons TAA, TAG or TGA. Sometimes multiple termination codons are placed at all reading frames to ensure effective translation termination from all reading frames.

A terminator is required for transcription termination and poly A addition for eukaryote. It also provides stability of the RNA transcripts. A terminator often located at 3' end of a gene. However a terminator can be placed anywhere on a plasmids to prevent transcription leakage from upstream promoters. Examples of terminators include tHP, T7, and rrnB from prokaryote, TK, BGH, and SV40 poly A addition sites from eukaryote.

Plasmids may be introduced into host cells by various methods known in recombinant techniques. In one preferred embodiment, calcium chloride method is used. In another preferred embodiment, rubidium chloride method is used. In a further preferred embodiment, electroporation method is used. As those skilled in the art will recognize, host cells containing these plasmids can be produced by a number of means such as transformation, transduction, transfection, conjugation, and the like.

Plasmid amplification and protein expression may be performed using standard recombinant DNA techniques as taught herein or as known in the art. Many of the techniques are described in J. Sambrook et al., Molecular cloning: A Laboratory Manual, Cold Spring Harbor Laboratory, Cold Spring Harbor, N.Y., 1989, Coligan et al., Current Protocols in Protein Science, Current Protocols, U.S.A., 1995, and Ausubel et al., Current protocols in Molecular Biology, Current protocols, U.S.A. 1994.

Host cells containing various plasmids may be used to aid other protein expression as known in the art. In one preferred embodiment, host cells containing plasmids aid the yield of a target protein expression. In another preferred embodiment, host cells containing plasmids aid the solubility of a target protein expression. In a further preferred embodiment, host cells containing plasmids modify the expressed target protein. In yet another preferred embodiment, host cells containing plasmids stabilize the expressed target protein.

It should be understood that not all functional DNA fragments would function equally well for a particular application. Neither will all host cells function equally well with the same plasmid. However, one of ordinary skill in the art may make a selection among the DNA fragments and host cells using the guidance provided herein without undue experimentation and without departing from the scope of the present invention.

The invention is described in further detail in the following non-limiting examples.

EXAMPLE 1

Construction of a De Novo Synthesized Plasmid

Prepare a linear DNA fragment containing replication origin.

Oligos 1 and 4 (sequence ID NOS: 1 and 4) were synthesized for replication origin based on pACYC 177 (Chang et al., J. Bacteriol., 134, 1141-1156 (1978)). Polymerase chain reaction (PCR, Mullis et al., and U.S. Pat. No. 4,683,202) was used to generate DNA fragments containing the replication origin. One nanogram of pACYC177 was used as templates. One microgram each of oligos were used as primers in each reaction. Total volume of each reaction was 100 microliters. Five units of Taq DNA polymerase were used in each reaction. The following temperature was indicated in Celsius. PCR were performed at cycling condition of 94 degree for 30 seconds, 68 degree for 2 minutes, and 72 degree for 2 minutes. These cycling conditions were repeated for 40 times. The reactions were kept at 72 degree for 5 minutes. Then the reactions were hold at 4 degree. The PCR product was verified by agarose gel electrophoresis. The replication origin on this DNA fragment was arbitrarily named origin 4 (4).

Prepare a linear DNA fragment containing selection marker gene.

Oligos 7 and 11 (sequence ID NOS 7 and 11) were synthesized for selection marker gene conferring tetracycline resistance. PCR was used to prepare the tetracycline selection marker gene using pBR 322 as a template (Bolivar et al., Gene 2, 75-93 (1977)). The PCR conditions were same as described above. The selection marker gene on this DNA fragment was named tetracycline (T).

The DNA fragments containing replication origin and selection marker gene were prepared. None of these DNA fragments alone can confer both autonomous DNA replication and host cell selection. Linker sequences were designed on each of these oligos to facilitate cloning. Only G and C bases are designed in the linker to give stable annealing. A Sma I site is designed on one of these linker sequences. The Sma I site can be used to linearize the plasmid in the future.

DNA fragments containing above described replication origin and selection marker gene were combined together by exonuclease III mediated cloning (Li et al., Nucleic Acid Res. 25:4165-4166 (1997)) to form a de novo synthesized plasmid. The combined DNA fragments were transformed into DH5a cells. The transformed cells were selected on Luria-Berani (LB) agar plate containing 12.5 microgram per milliliter tetracycline. The size of the plasmid was verified by restriction digestion and agarose gel electrophoresis. The de novo synthesized plasmid was named p4T since it is made from replication origin 4 (4) and tetracycline (T) selection marker. Schematic diagrams of construction of the de novo synthesized p4T are shown on FIG. 1.

EXAMPLE 2

Construction of Other De Novo Synthesized Plasmids

Sixty de novo synthesized plasmids were constructed as described above. Ten of them were used in the future plasmid construction. They are p1A, p3A, p1C, p2C, p3C, p4C, p2T, p4T, p2K, and p4K (sequence ID NOS: 32 to 41). The Arabic number of the plasmid represents its replication origin and the capital letter of the plasmid represents its selection marker gene. For example the plasmid p4C contains replication origin 4 and selection marker gene resistant to chloramphenicol. These plasmids are the smallest known plasmids containing same replication origins and selection marker genes. Since the odd numbered plasmids contain replication origins based on ColE1 and the even numbered plasmids contain replication origins based on p15A, the odd numbered plasmids should be compatible with the even numbered plasmids. Plasmids based pBR322 and p15A replication origins should be low copy number plasmids and plasmids based on pUC19 replication origin should be high copy number plasmids.

Figure 2:
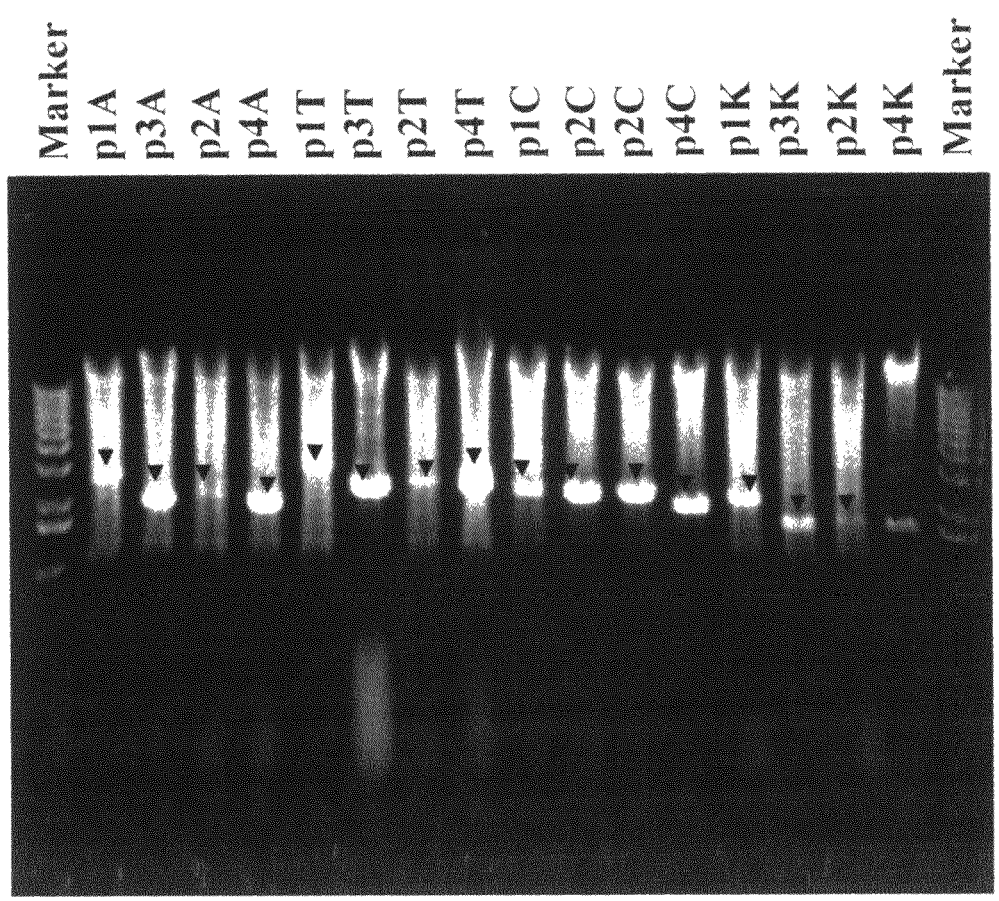
FIG. 2. Plasmid p4T is a high copy number plasmid. The replication origin of p4T is derived from low copy number replication origin p15A. However its copy number is comparable to high copy number plasmid pUC19 derived plasmids p3A, p3T, and p4K. The name of each plasmid is indicated above each lane of the gel. The arrow on the gel indicates approximate position of the linearized plasmid.

It is surprising to find that p4T is a high copy number plasmid since replication origin 4 is based on p15A replication origin which is considered to be a low copy number origin (Sambrook et al., Molecular cloning: A Laboratory Manual, Cold Spring Harbor Laboratory, Cold Spring Harbor, N.Y., Vol. 1, pp.1.3-1.5, (1989)). Sixteen de novo synthesized plasmids were prepared under same conditions. They are linearized by Sma I restriction digestion and run on 0.8% agarose gel. The picture of this gel is shown on FIG. 2. The names of these plasmids are listed above the gel. The marker is 1 Kb DNA Ladder (Life Technologies, Rockville, Md.). The arrow on the gel indicates approximate position of the linearized plasmid. Consistence with prior art teaching, p2A, p2T, and p2K are low copy number plasmids since their replication origins are based on p15A origin. Surprisingly, the copy number of p4T is comparable with plasmids p3A, p3T, and p3K based on high copy number plasmid pUC19.

Restriction sites such as BamH I, EcoR I, EcoR V, Hind III, Cla I, Pst I, Nco I, Nde I, Nsi I, Pvu II, Sca I, Sal I, Sph I, Sma I, and Xho I on these plasmids were mutated by site directed mutagenesis (Current protocols in Molecular Biology, Ausubel et al., Current protocols, U.S.A., (1994)).

Oligos 1 to 4 (sequence ID NOS: 1 to 4) were synthesized for replication origins of these ten plasmids. Replication origins of CoE1 based pBR322 (Bolivar et al., Gene 2, 75-93 (1977)) and pUC19 (Vieira et al., Gene 19, 259-268 (1982)) and p15A based pACYC177 (Chang et al., J. Bacteriol., 134, 1141-1156 (1978)) were used in the experiments. The sequences required for these replication origins are described in the previous papers (Bird et al., J. Bacteriol., 145, 1305-1308 (1981), Stuber et al., Proc. Natl. Acad. Sci. USA, 78, 167-171 (1981), Marians et al., J. Biol. Chem., 257, 5656-5662 (1982), Selzer et al., Cell 32, 119-129 (1983)). PCR with oligo 2, oligo 4, and pBR322 produced replication origin 1 DNA fragment based on ColE1. PCR with oligo 3, oligo 4, and pACYC177 produced replication origin 2 DNA fragment based on p15A. PCR with oligo 1, oligo 4, and pUC19 produced replication origin 3 DNA fragment based on ColE1. PCR with oligo 1, oligo 4, and pACYC177 produced replication origin 4 DNA fragment based on p15A.

Oligos 5 to 12 (sequence ID NOS: 5 to 12) were synthesized for selection marker genes of these ten plasmids. Antibiotics resisted by host cells containing these selection marker genes are ampicillin, tetracycline, chloramphenicol, and kanamycin. The promoters and terminators of these selection marker genes were studied in the previous papers (Stuber et al., Proc. Natl. Acad. Sci. USA, 78, 167-171 (1981), Brosius et al., J. Biol. Chem., 257, 9205-9210 (1982), Sheflin et al., Nucleic Acid Res., 13, 6137-6154 (1985), Smith et al., Gene 84, 159-164 (1989)). Oligos 5 to 12 were designed according to these studies. PCR with oligo 5, oligo 9, and pUC19 produced ampicillin DNA fragment that will confer ampicillin resistance. PCR with oligo 8, oligo 12, and pACYC184 produced chloramphenicol DNA fragment that will confer chloramphenicol resistance. PCR with oligo 7, oligo 11, and pBR322 produced tetracycline DNA fragment that will confer tetracycline resistance. PCR with oligo 6, oligo 10, and pACYC177 produced kanamycin DNA fragment that will confer kanamycin resistance.

EXAMPLE 3

Construction of Other Plasmids Generated From De Novo Synthesized Plasmids

Hundreds of other plasmids are generated from the ten de novo synthesized plasmids described above. Construction of p4TI3E and p2CIXL will be described as examples below. Plasmid p4TI3E contains replication origin 4 (4), a selection marker gene resistant to tetracycline (T), a LacI gene repressing a promoter containing LacI operator (I), an artificial transcription unit 3 (3), and DNA sequences encoding GroEL and GroES proteins (E). Plasmid p2CIXL contains replication origin 2 (2), a selection marker gene resistant to chloramphenicol(C), a LacI gene repressing a promoter containing Lac I operator (I), and human retinoid X receptor beta ligand binding domain (XL, Marks et al., EMBO J. 11, 1419-1435 (1992)).

Oligos 13 and 14 (sequence ID NOS: 13 and 14) were synthesized for LacI gene (Farabaugh, Nature 274, 765-769 (1978)). One nanogram of pGEX-3X (Smith et al., Gene 67, 31-39 (1988)) was used as template. The PCR condition was same as that used for replication origins and selection marker genes. The PCR product was cloned into Sma I site of p4T to make plasmid p4TI.

Oligos 15 to 24 (sequence ID NOS: 15 to 24) were synthesized for the artificial transcription unit 3. Oligos 15 to 24 were mixed at concentration of 10 nanogram per microliter. 10 microliters of this oligo mix was used for first PCR with 5 microliter water, 2 microliter PCR buffer, 3 microliter 1 mM dNTPs, and 1 unit Taq DNA polymerase. The PCR was performed at cycling conditions of 94 degree for 30 seconds, 68 degree for 30 seconds, and 72 degree for 30 seconds. These cycling conditions were repeated for 40 times. The reaction was kept at 72 degree for 5 minutes. Then the reaction was hold at 4 degree. Five microliters of this PCR product was used as template for second PCR. Second PCR was performed with 1 microgram each of oligo 15 and 24, 5 microliters of 1 mM dNTPs, and 5 units of Taq in total volume of 50 microliters. The cycling conditions were same as the first PCR. The artificial transcription unit 3 (sequence ID NO: 25) was obtained. Terminator tHP (Nohno et al., J. Bacteriol. 170, 4097-4102 (1988)) was placed at the 5' end of the transcription unit to prevent transcription leakage from upstream promoters. The promoter, terminator, and ribosome binding site of bacterial phage T7 gene 10 (Dunn et al., J. Mol. Biol., 166, 477-535 (1983)) were used in the transcription unit for high level protein expression. LacI operator sequences (Calos, Nature 274, 762-765 (1978)) were placed immediately after the T7 promoter. With another LacI operator located at 3' end of LacI gene, these operators will assure minimum basal level expression and maximum induction upon adding IPTG. Multiple cloning sites were placed after the ribosome binding site. These multiple cloning sites contain Nde I, Hind III, Sma I, Kpn I, Sal I, Spe I, and Hpa I restriction sites. Multiple stop codons are present in all reading frames after the multiple cloning sites. Two linkers of 12 nucleotides each were placed at 5' and 3' ends of the artificial transcription unit 3. The transcription unit 3 was cloned into Sma I site of plasmid p4TI to generate p4TI3.

Figure 3:
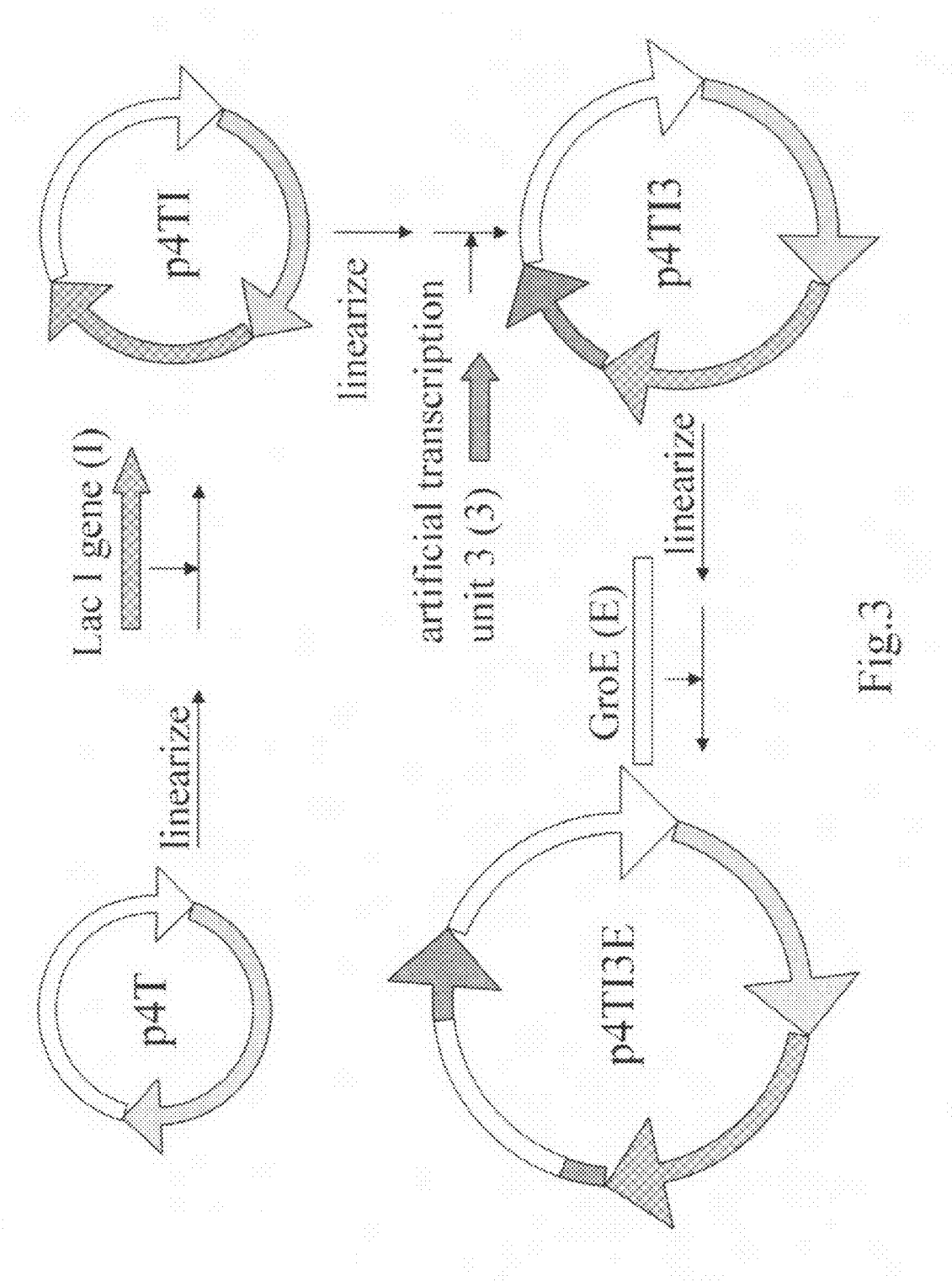
FIG. 3. Schematic diagram of construction of plasmids or p4TI, p4TI3, and p4TI3E from a de novo synthesized plasmid p4T. The arrow indicates the direction of transcription.

Oligos 26 to 29 (sequence ID NOS: 26 to 29) were synthesized for GroE gene (Hemmingsen et al., Nature 333, 330-334 (1988)). Two proteins GroES and GroEL are encoded by GroE gene. One microgram each of oligos 26 and 27 with 0.1 microgram of genomic DNA of E. coli strain W3110 were used for first PCR. The PCR was performed with 1 unit each of Taq and Vent DNA polymerase (New England Biolabs, Beverly, Md.) in total volume of 20 microliters. Cycling conditions were 94 degree for 30 seconds, 60 degree for 30 seconds, and 72 degree for 2 minutes. These cycling conditions were repeated for 60 times. The reaction was kept at 72 degree for 5 minutes. Then the reaction was hold at 4 degree. One microliter of the PCR product was used for second PCR. Second PCR was performed with 1 microgram each of oligo 28 and 29, 10 microliters of 1 mM dNTPs, and 1unit each of Taq and Vent in total volume of 50 microliters. The cycling conditions were same as the first PCR. This PCR product was cloned into the Nde I and Sal I sites of plasmid p4TI3 to generate p4TI3E. The schematic diagrams of these plasmid construction are shown on FIG. 3.

Oligos 30 and 31 (sequence ID NOS: 30 and 31) were synthesized to make p2CXL. Ten nanograms of pET-15b-RXR LBD (Li et al., Proc. Natl. Acad. Sci. USA 94, 2278-2283 (1997)) was used as template in the PCR. One microliter each of 50 uM oligos 30 and 31, 1 unit each of Taq and Pfu (Stratagene, La Jolla, Calif.), and 6 microliters of 1 mM dNTPs were used in the total volume of 20 microliters. Cycling conditions were 94 degree for 45 seconds, 68 degree for 30 seconds, and 72 degree for 2 minutes. These cycling conditions are repeated for 35 times. Then the reaction was hold at 4 degree. The PCR product was cloned into Sma I site of p2C to make p2CXL.

EXAMPLE 4

Protein Expression of Plasmids Generated From De Novo Synthesized Plasmids

Figure 4A:
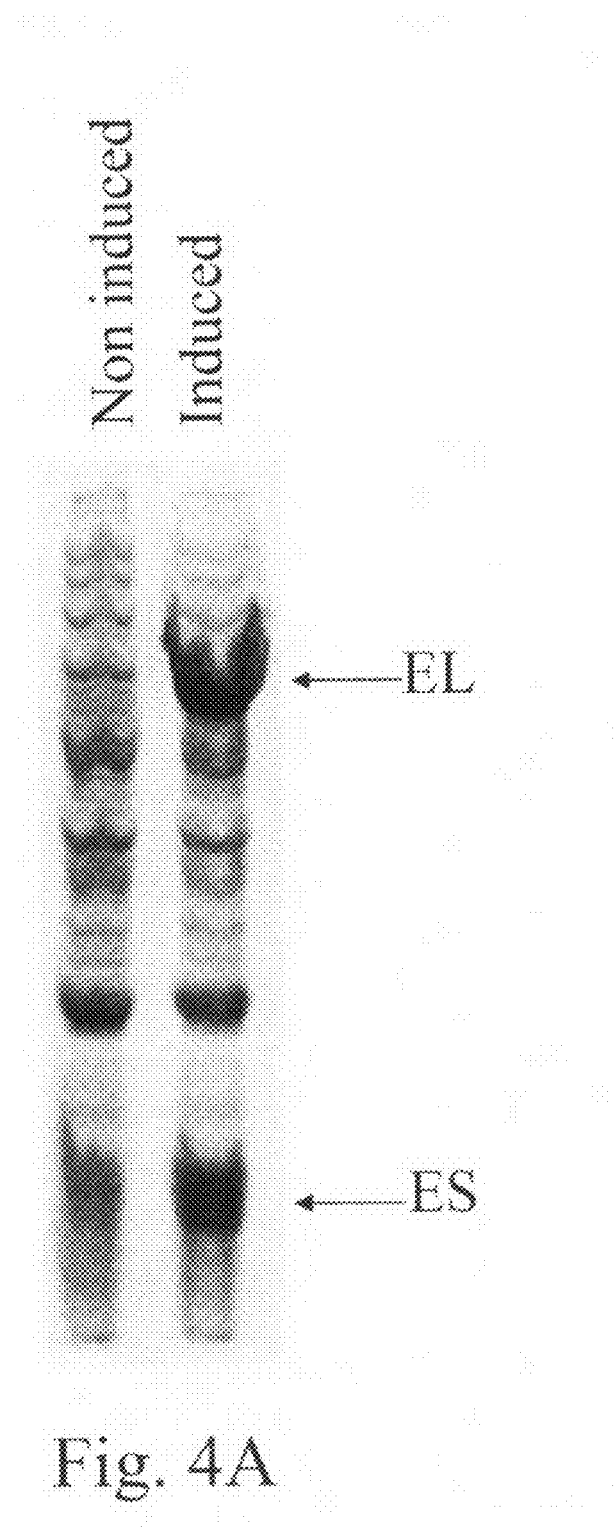
FIG. 4A shows both proteins EL and ES were expressed from induced sample containing p4TI3E.
Figure 4B:
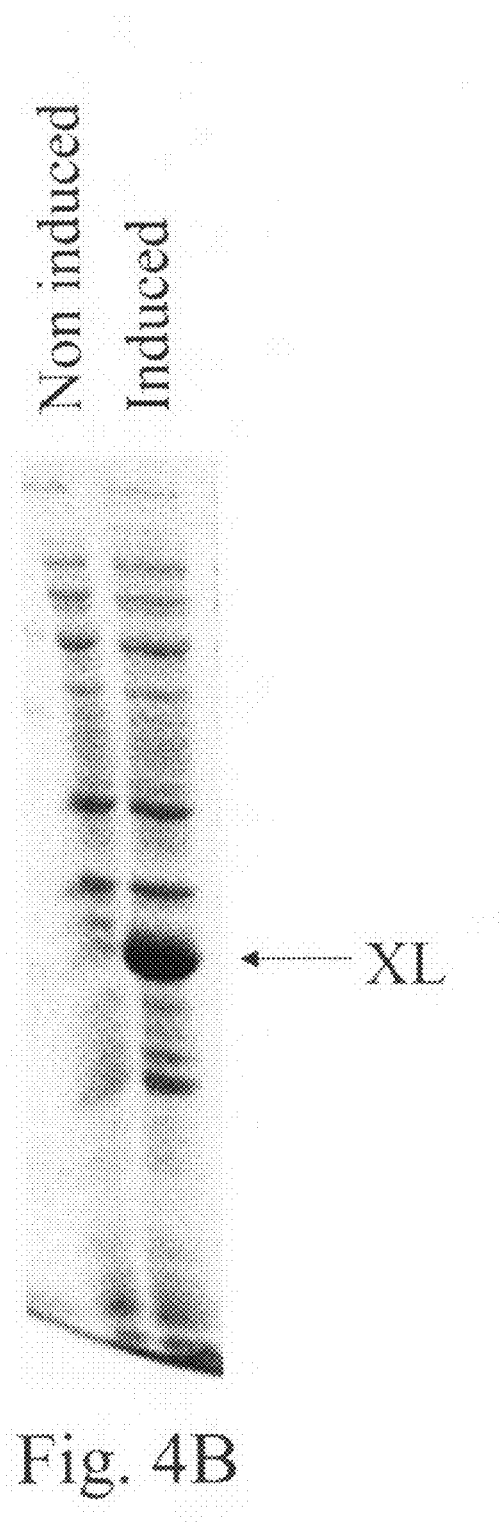
FIG. 4B shows protein XL was expressed from induced sample containing p2CXL.

Plasmids p4TI3E and p2CXL were introduced to *E. coli* strain BL21 (DE3) by calcium chloride method. Colonies containing these plasmids were obtained from LB agar plates containing ampicillin or chloramphenicol respectively. One colony from each plate was inoculated into LB media. Incubate them at 37 degree with shaking for 3 to 5 hours until their OD600 reaches 0.4 to 1.0. Take out 100 microliters each as non-induced sample. Add IPTG to final concentration of about 1 mM/ml. Incubate them at 37 degree with shaking for 1 hour 40 minutes and 2 hour 30 minutes respectively. Take out 100 microliters each as induced sample. Spin down the non-induced and induced samples at 14,000 RPM for 1 minute. Resuspend the cell pellets in 20 µl 1×SDS buffer. Boil them for 3 minutes. Load 5 microliters each on 12% Tris-glycine SDS gel. After electrophoresis, the gel was stained for 10 minute with Coomassie blue staining solution (0.25% Coomassie brilliant blue R-250, 10% acidic acid, 45% methanol). Detain the gel with 7.5% methanol and 5% acidic acid overnight (about 16 hours). Both proteins GroEL (EL) and GroES (ES) were expressed from induced sample of *E. coli* cells containing p4TI3E (FIG. 4A). Protein RXR LBD (XL) was expressed from induced sample of *E. coli* strain containing p2CXL (FIG. 4B).

EXAMPLE 5

Figure 5:
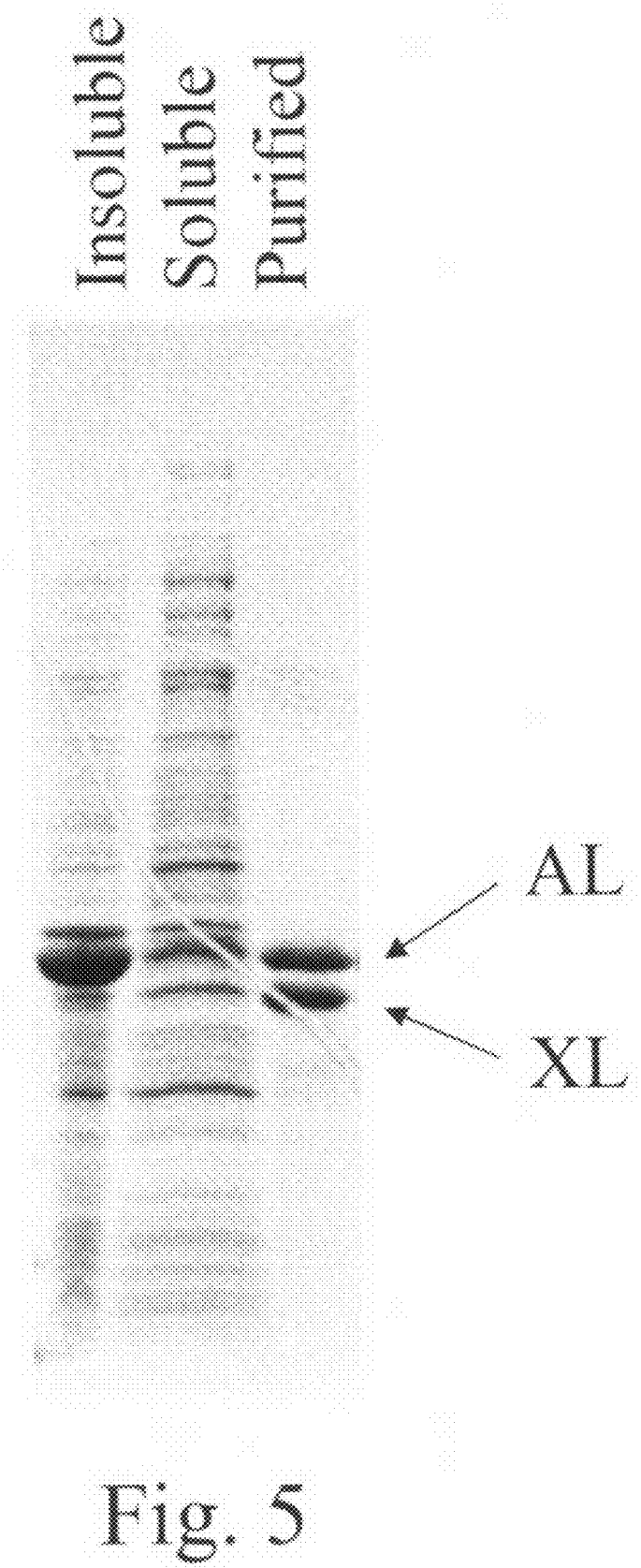
FIG. 5. Host cells containing p4CXL aid the solubility of AL. Protein AL is not soluble when it is expressed by itself. It becomes soluble when it is expressed in the host cell containing p4CXL, which is generated from a de novo synthesized plasmid p4C.

Host Cells Containing Plasmids Generated From the De Novo Synthesized Plasmid Aid the Solubility of Another Protein That is Not Soluble When Expressed By Itself A plate of host cells containing p2CXL plasmids were obtained from EXAMPLE 3. Host cells containing plasmid pET-15b-RAR-LBD (Li et al., Proc. Natl. Acad. Sci. USA 94, 2278-2283 (1997)) were plated on a Laurie Broth agar plate with ampicillin. Plasmid pET-15b-RAR-LBD was introduced into the host cells containing p2CXL. Plasmids p2CXL and pET-15b-RAR-LBD contain compatible replication origins and different selection markers (ampicillin and chloramphenicol). Therefore they can be selected and co-exist in one cell. The cells were grown on plate containing both ampicillin and chloramphenicol. Host cells containing p2CXL and pET-15b-RAR-LBD were grown on plates containing chloramphenicol and ampicillin respectively. One colony from each plate was picked up and inoculated into LB media with appropriate antibiotic(s). The concentrations of ampicillin and chloramphenicol are 50 mM per milliliter (mM/ml) and 35 mM/ml respectively. These cultures were incubated at 37 degree with shaking until their OD600 reaches 0.4 to 1.0. The cultures were induced by IPTG at final concentration of 1 mM/ml for 2 hours and 30 minutes. The cells were harvested and sonicated in HKI buffer (20 mM Hepes, pH 8.0, 100 mM KCL, 20 mM imidazole). Soluble and insoluble proteins were obtained from supernatants and pellets respectively. Binding to nickel agarose beads and by washing multiple times with HKI buffer purifies these proteins. The soluble, insoluble, purified proteins were loaded on Tris-glycine SDS gels. After electrophoresis, the gels were stained, destained, and dried between cellophane membranes. It has been shown that RXR LBD (XL) is soluble and RAR LBD (AL) is largely insoluble and can hardly purified when they expressed individually (Li et al., Proc. Natl. Acad. Sci. USA 94, 2278-2283 (1997)). Significant amount of AL becomes soluble and purified when it is expressed in the host cells containing p2CXL plasmids (FIG. 5). Therefore host cells containing plasmids p2CXL generated from the de novo synthesized p2C aid the solubility of AL.

All publications mentioned hereinabove are hereby incorporated their entirety by reference.

While the foregoing invention has been described in some detail for purpose of clarity and understanding, it will be appreciated by one skilled in the art from a reading of this disclosure that various changes in form and detail can be made without departing from the true scope of the invention and appended claims.

What is claimed is:

1. A synthesized plasmid comprising the DNA sequence defined by SEQ ID NO: 37.
2. A DNA fragment comprising the plasmid according to claim 1.
3. A DNA vector comprising the plasmid according to claim 1.
4. A bacterial cell strain comprising the DNA vector according to claim 3.
5. A eukaryotic cell line comprising the DNA vector according to claim 3.

* * * * *